(12) United States Patent
Ha et al.

(10) Patent No.: US 12,420,256 B2
(45) Date of Patent: Sep. 23, 2025

(54) DIELECTRIC BARRIER DISCHARGE PLASMA REACTOR COMPRISING MACROPOROUS SILICA AS DIELECTRIC MATERIAL

(71) Applicants: Sogang University Research & Business Development Foundation, Seoul (KR); Korea Advanced Institute of Science and Technology, Daejeon (KR)

(72) Inventors: Kyoung-Su Ha, Hanam-si (KR); Jinwoo Lee, Daejeon (KR); Juchan Kim, Daegu (KR); Namheon Lee, Seoul (KR); Seongseop Kim, Daejeon (KR); Yeongkwang Bae, Cheongju-si (KR)

(73) Assignees: Sogang University Research & Business Development Foundation, Seoul (KR); Korea Advanced Institute of Science and Technology, Daejeon (KR)

(*) Notice: Subject to any disclaimer, the term of this patent is extended or adjusted under 35 U.S.C. 154(b) by 0 days.

(21) Appl. No.: 17/074,732

(22) Filed: Oct. 20, 2020

(65) Prior Publication Data
US 2021/0260558 A1 Aug. 26, 2021

(30) Foreign Application Priority Data
Feb. 26, 2020 (KR) .................. 10-2020-0023773

(51) Int. Cl.
*B01J 19/08* (2006.01)
*B01J 21/06* (2006.01)
(Continued)

(52) U.S. Cl.
CPC ........... *B01J 19/088* (2013.01); *B01J 21/063* (2013.01); *B01J 21/08* (2013.01); *C07C 2/80* (2013.01);
(Continued)

(58) Field of Classification Search
CPC ........ B01J 21/08; B01J 19/088; B01J 21/063; B01J 2219/0809; B01J 2219/0815;
(Continued)

(56) References Cited

U.S. PATENT DOCUMENTS 8,993,474 B2* 3/2015 Choi .................... B01J 35/1042
502/227
2003/0141182 A1* 7/2003 Kong .................... B01J 19/088
204/170
(Continued)

FOREIGN PATENT DOCUMENTS

CN 102408095 * 4/2012
JP H 05-345685 A 12/1993
(Continued)

OTHER PUBLICATIONS

Taheraslani et al. (Energies 2020, 13, 468), "Coupling of CH4 to C2 Hydrocarbons in a Packed Bed DBD Plasma Reactor: The Efect of Dielectric Constant and Porosity of the Packing" (Year: 2019).*
(Continued)

*Primary Examiner* — Xiuyu Tai
(74) *Attorney, Agent, or Firm* — DALY, CROWLEY, MOFFORD & DURKEE, LLP

(57) ABSTRACT

The present invention relates to a dielectric barrier discharge (DBD) plasma reactor for the preparation of $C_{2+}$ hydrocarbons from methane, wherein the DBD plasma reactor comprises macroporous silica, as a dielectric material, and optionally a photocatalyst that is impregnated into the pores of the macroporous silica.

1 Claim, 19 Drawing Sheets

(51) Int. Cl.
*B01J 21/08* (2006.01)
*C07C 2/80* (2006.01)

(52) U.S. Cl.
CPC .............. *B01J 2219/0809* (2013.01); *B01J 2219/0815* (2013.01); *B01J 2219/0875* (2013.01); *B01J 2219/0896* (2013.01); *C07C 2521/06* (2013.01); *C07C 2521/08* (2013.01)

(58) Field of Classification Search
CPC ........ B01J 2219/0875; B01J 2219/0896; B01J 19/2415; B01J 19/123; B01J 2219/0843; B01J 2219/0869; B01J 2219/0894; B01J 2219/0841; B01J 2219/0884; B01J 2219/00135; B01J 2219/0871; B01J 2208/025; B01J 2219/083; B01J 2219/0892; C07C 2/80; C07C 2521/08; C07C 2521/06; C07C 29/50; C07C 27/12; H05H 1/24; H05H 1/245; H05H 1/2465; H05H 1/2406; H05H 2245/17; H05H 2240/20; C10G 47/12; C10G 69/02; C10G 15/08; C10G 32/02; C10G 65/12; C10G 45/04; C01B 2203/0861; C01B 3/342

See application file for complete search history.

(56) References Cited

U.S. PATENT DOCUMENTS

| | | | |
|---|---|---|---|
| 2006/0150676 | A1 | 7/2006 | Kim et al. |
| 2016/0362351 | A1* | 12/2016 | Nagaki ............... B01J 23/745 |
| 2021/0094000 | A1* | 4/2021 | Bernadet ............. B01J 21/08 |

FOREIGN PATENT DOCUMENTS

| | | |
|---|---|---|
| JP | 2004-244270 A | 9/2004 |
| JP | 2005-144445 A | 6/2005 |
| JP | 2015-145323 A | 8/2015 |
| KR | 10-2004-0106791 A | 12/2004 |
| KR | 10-0981360 B1 | 9/2010 |
| KR | 2015-0078105 A | 7/2015 |

OTHER PUBLICATIONS

Zheng et al. (Journal of Power Sources 274, 2015, 286-294). "Plasma-assisted catalytic dry reforming of methane: Highly catalytic performance of nickel ferrite nanoparticles embedded in silica" (Year: 2015).*
Li et al. (Applied Catalysis B: Environmental 261, 2020, 118228), "Direct conversion of CO2 and CH4 into liquid chemicals by plasma-catalysis" (Year: 2020).*
Lopez-Munoz et al. (Catalysis Today 101, 2005, 307-314), "Role of the support on the activity of silica-supported TiO2 photocatalysts: Structure of the TiO2/SBA-15 photocatalysts" (Year: 2005).*
Liu et al. (J. Phys. Chem. C 2014, 118, 10686-10693), "Nonoxidative Conversion of Methane in a Dielectric Barrier Discharge Reactor: Prediction of Reaction Performance Based on Neural Network Model" (Year: 2004).*
Li S et al. (Chemical Engineering Journal 388, 2020, 124275), "The application of dielectric barrier discharge non-thermal plasma in VOCs abatement: A review" (Year: 2020).*
Kim et al., "Plasma-Assisted Methane Coupling to Produce Ethane Over TiO2/Macroporous Silica Catalysts;" Proceedings of Abstract Book, The 8th Asia-Pacific Congress on Catalysis; Aug. 4-7, 2019; 23 Pages.
Kim et al., "Plasma-Assisted Catalytic Effects of $TiO_2$/Macroporous $SiO_2$ on the Synthesis of Light Hydrocarbons from Methane;" Article from ChemCatChem; Published Jun. 28, 2020; 10 Pages.
Kim et al., "Plasma-Assisted Catalytic Effects of $TiO_2$/Macroporous $SiO_2$ on the Synthesis of Light Hydrocarbons from Methane;" Supporting Information from ChemCatChem; Jun. 28, 2020; 11 Pages.
Korean Office Action (with Machine English Translation from Espacenet.com) dated Oct. 23, 2021 for Korean Application No. 10-2020-0023773; 13 Pages.
Korean Notice of Final Rejection (with English Translation) dated Aug. 18, 2022 for Korean Application No. 10-2020-0023773; 10 Pages.

* cited by examiner

[a] Weight of coke (g) = Weight of bed (g)×[1-Weight loss (-)] (where, weight loss was obtained by TGA method.)
[b] Cumulative weight of $C_{5+}$ hydrocarbon products (g) = Mass flow rate of methane (g/min)×Yield of average $C_{5+}$ products (-)×Reaction time (min)

DIELECTRIC BARRIER DISCHARGE PLASMA REACTOR COMPRISING MACROPOROUS SILICA AS DIELECTRIC MATERIAL

CROSS REFERENCE TO RELATED APPLICATIONS

This present application claims the benefit of priority to Korean Patent Application No. 10-2020-0023773 filed on Feb. 26, 2020 in the Korean Intellectual Property Office. The disclosure of the above-listed application is hereby incorporated by reference herein in its entirety.

TECHNICAL FIELD

The present invention relates to a dielectric barrier discharge (DBD) plasma reactor for the preparation of $C_{2+}$ hydrocarbons from methane, wherein the DBD plasma reactor comprises macroporous silica, as a dielectric material, and optionally a photocatalyst that is impregnated into the pores of the macroporous silica.

BACKGROUND ART

The production of basic olefin compounds (e.g., ethylene, propylene, and butylene) is very important in the chemical, petrochemical, and biochemical industries. In the past, these olefins were mostly obtained by treatment of petroleum and coal. The development of non-traditional natural gas sources, particularly in North America, has transformed the core technology of production and product markets. One of the most representative technologies, excluding the prior art based on oil and coal, is an ethane cracking technology which converts ethane to olefins (e.g., ethylene, propylene, etc.) at a high temperature using natural gas liquids (NGLs) containing ethane. In ethane cracking centers (ECCs), the above technology is not a new-to-world technology. Such a production technology has long been practiced, especially in the Middle East, due to the low cost of natural gas sources. The ECCs are known to produce ethylene in a very high yield, but the feed mixture is limited to NGLs (e.g., ethane, propane, butane, and other $C_{2+}$ hydrocarbons.

Therefore, researchers in the corresponding field are making efforts to develop a new process capable of utilizing methane, which accounts for most of the traditional and non-traditional natural gas sources, including the well-known shale gas. Since 1982, a breakthrough conversion technology known as the oxidative coupling of methane (OCM) has been developed, and it has recently been rediscovered in many aspects due to the shale gas boom. Despite the fact that two methane molecules can bind under oxidative conditions and produce ethylene and ethane with a maximum yield of 25% $C_2$ compounds, there is a disadvantage in that the yield decreases due to a side reaction to $CO_x$ and an energy-intensive reaction at 800° C. or higher. In the case of using pure oxygen in the oxidative reaction, the most difficult part is the separation of oxygen from the air. This separation is usually performed by cryogenic distillation, which requires much electricity. In addition, this separation may be performed in combination with pressure swing adsorption (PSA) and membrane separation methods. Meanwhile, when air is used as an oxidant feed instead of pure oxygen, a post-treatment unit is required for the separation of nitrogen and other gases from the product mixture. As such, in both processes, an additional gas separation step may be required depending on the structure of the process and the type of catalyst. In order to resolve the inconvenience of this process, a non-oxidative method for synthesizing ethylene and aromatic compounds has recently been introduced. However, this method may require not only an energy-intensive process during the separation process but also the synthesis reaction. For example, the synthesis is performed at a high temperature of around 1,000° C., and the catalyst is prepared at a much higher temperature (about 1,700° C.) so as to form a single site catalyst.

Meanwhile, macroporous silica is being applied not only to separation, membranes, adsorption, and catalysts, but also to the field of catalyst supports due to its large pore volume and rapid mass transfer. The typical inverse opal method for the production of macroporous silica requires a complex multi-step process associated with separation. Unlike the inverse opal method, the sol-gel method accompanied by macrophase separation provides a direct access to well-defined macroporous structures, and this is induced by spinodal decomposition between the gel-rich phase and the solvent-rich phase during the inorganic polymerization process. Therefore, through this approach, it is possible to prepare well-developed double-continuous macropores with tunable properties (e.g., size and structure of pores).

Further, in order to develop an industrially applicable method, it must be possible to eliminate or avoid carbon deposition. In consideration of regeneration, three or four methods may be applied to a heterogeneous reaction system. In order to understand the regeneration, a propane dehydrogenation process may be used as an example. Specifically, in the catalyst moving bed of Oleflex (UOP), regeneration is performed by a continuous catalytic regenerator (CCR). The catalyst used is sent to the CCR unit for regeneration and reuse. In a similar manner, it has been reported that catalyst particles can be regenerated using a separate regeneration reactor connected to a primary fluidized-bed type reactor for the main reaction. With respect to the fixed layer, as performed in the Catofin process by Lummus technology, the deactivated catalyst particles can be regenerated in situ by a cyclic regeneration method. Such a process employs reactors in parallel and is operated in a cyclic manner.

SUMMARY

The present inventors, in designing a reactor for producing $C_{2+}$ hydrocarbons by a non-oxidative coupling reaction of methane performed at room temperature and ambient pressure, have made extensive efforts to provide conditions under which the methane coupling reaction with reduced coke production is possible as well as a product with a desired composition that can be obtained by controlling the shape and/or composition of the dielectric material being filled into a reactor. As a result, they have confirmed that when macroporous silica is used as a dielectric material, it is possible to significantly alleviate the problem of a pressure difference that occurs when the existing powdered dielectric material is used, even if the macroporous silica is used in a non-pelletized state, and further that when a photocatalyst (e.g., $TiO_2$ nanoparticles, etc.) is additionally impregnated into the pores of the macroporous silica, coke production is reduced, and correspondingly, $C_{5+}$ hydrocarbon production is increased, thereby completing the present invention.

The present invention provides a dielectric barrier discharge (DBD) plasma reactor for preparing $C_{2+}$ hydrocarbons from methane, which comprises: a dielectric tube; macroporous silica, which is filled into the whole or a part of the dielectric tube; a ground electrode, which encompasses the whole or a part of a region of the dielectric tube into which the macroporous silica is filled; and a powered electrode, which is spaced apart from the inner wall of the dielectric tube at a predetermined interval in parallel, and is inserted so as to penetrate the whole or a part of the macroporous silica layer that is filled into the dielectric tube.

Hereinafter, the present invention will be described in detail.

The present invention is designed to provide a reactor, which, in a non-oxidative coupling reaction of methane performed using a DBD plasma reactor filled with a dielectric material, is capable of not only preventing occurrence of a pressure difference as the reaction proceeds and the content of saturated hydrocarbons in the product from being relatively lowered, when the filled dielectric material is powder, but also excluding the inconvenience of a pelletizing process or physical and/or chemical changes that may occur due to palletization; and maintaining a low pressure difference, exhibiting excellent methane conversion and ethane selectivity, and exhibiting an improved mass transfer rate, which is an advantage of a pelletized catalyst. The present invention is based on the discovery that by using macroporous silica, which is not a catalyst in the form of powder or a pellet, as a dielectric material to be filled into the reactor, it is possible to achieve the advantageous effects described above as well as minimizing the disadvantages that may occur when a catalyst in the form of powder or a pellet is used without an additional process.

The present invention provides a dielectric barrier discharge (DBD) plasma reactor for preparing $C_{2+}$ hydrocarbons from methane, which comprises: a dielectric tube; macroporous silica, which is filled into the whole or a part of the dielectric tube; a ground electrode, which encompasses the whole or a part of a region of the dielectric tube into which the macroporous silica is filled; and a powered electrode, which is spaced apart from the inner wall of the dielectric tube at a predetermined interval in parallel, and is inserted so as to penetrate the whole or a part of the macroporous silica layer that is filled into the dielectric tube.

The dielectric tube used in the DBD reactor of the present invention may be a cylindrical tube made of alumina or quartz, but the material or shape of the dielectric tube is not limited thereto, and various dielectric barrier materials (e.g., components constituting a conventional DBD plasma reactor) may be used without limitation.

For example, the dielectric tube included in the DBD reactor of the present invention may be a tube in which both ends are closed so that the free entry of unwanted gases can be prevented. Further, the dielectric tube is configured such that a gas inlet for impregnating methane is connected to one side of the dielectric tube and a gas outlet is connected to the other side of the dielectric tube with respect to the region filled with the macroporous silica. Therefore, the reaction is performed in such a manner that the dielectric tube passes through the macroporous silica layer filled with impregnated reactants from one end, and the materials produced therefrom are discharged through the other end. In particular, optionally, the products can be immediately analyzed by connecting an analyzer (e.g., gas chromatography, etc.) to the gas outlet.

In the present invention, methane, which is a reactant to be impregnated into the reactor for the preparation of $C_{2+}$ hydrocarbons, may be impregnated as a mixture with an inert gas at a ratio of 1:9 to 7:3. For example, when the proportion of methane impregnated is less than 10%, the reaction may be performed inefficiently, while when the proportion of methane is in excess of 70%, the generation of coke as a by-product may increase. For example, as described above, by including an inert gas together, the products can be analyzed immediately by providing an on-line GC analyzer, etc. at the gas outlet side. Alternatively, a certain amount of hydrogen, etc. may be further included in addition to the inert gas, but the present invention is not limited thereto.

The DBD plasma reactor of the present invention may be used in performing a non-oxidative coupling reaction of methane at room temperature and ambient pressure. The non-oxidative coupling of methane provides $C_{2+}$ hydrocarbons as products as is the case of oxidative coupling, but it does not produce thermodynamically unstable combustion products. Additionally, since the non-oxidative coupling of methane can be performed through a non-thermal process, it does not require excessive energy to form reactive radicals. Further, since it can prevent decomposition of methane, which can occur at a high temperature, higher selectivity for $C_{2+}$ hydrocarbon products can be exhibited.

As used herein, the term "macroporous" refers to a property of a material having pores with an average diameter of 50 nm or more. For example, the macroporous silica, which is filled into the DBD plasma reactor of the present invention, may have pores with an average pore size of 50 nm to 50 μm, for example, an average pore size of 1 μm to 10 μm, but the average pore size is not limited thereto. For example, when the macroporous silica includes pores with an average diameter of less than 50 nm, there may be problems in that material transfer may not proceed smoothly or a pressure difference that occurs when a powder catalyst is used may occur. In contrast, when the pore size exceeds 50 μm, the density of the macroporous silica being filled becomes low and thus the amount of the filler becomes insufficient, and as a result, the reaction with the DBD plasma may be deteriorated. Alternatively, it may be possible that as the size of macropores increases, their surface area decreases, which is thus not advantageous to the dispersion of the catalyst; it may be difficult to uniformly control the size of the nanocrystals when the catalyst material is impregnated; or it may be possible that the occurrence of sintering, etc. is not excluded. Moreover, it may be disadvantageous in the formation of a micro-discharge within pores.

The DBD plasma reactor of the present invention, which prepares a $C_{2+}$ hydrocarbon product through a non-oxidative coupling reaction of methane using the same, can increase the content of paraffins in the $C_{2+}$ hydrocarbon product. For example, the $C_{2+}$ hydrocarbon product prepared by using the DBD plasma reactor of the present invention may show a paraffin fraction of 60% or more, specifically 70% or more, and more specifically 75% or more (the proportion of paraffins to the total sum of paraffins and olefins). When the fraction of a specific product is significantly high as such, it is easy to separate the product in the actual process, and thus, the efforts and costs required for the subsequent separation process can be reduced.

The macroporous silica to be filled into the DBD plasma reactor of the present invention may be in the form of a non-pelletized particle with an average diameter of 100 μm to 1,000 μm, but is not limited thereto.

In addition, since macroporous silica with large-sized pores is used in the reactor of the present invention as described above, no pressure difference occurs during the reaction even if it is filled in a state of non-pelletized particles, and has a characteristic that the pattern in methane conversion, product selectivity, or a paraffin content of the hydrocarbons produced for a reaction using the reactor is similar to that for a reaction using a reactor which is filled with a pelletized dielectric material.

For example, the DBD plasma reactor of the present invention can discharge by applying a low power of 30 W to 60 W. This indicates that the DBD plasma reactor can be operated with a low power which is lower than that consumed by a conventional incandescent lamp (60 W).

Specifically, the powered electrode, to which a high voltage is applied in the DBD plasma reactor of the present invention, can be connected to an alternating current (AC) power supply. The alternating current (AC) applied to the powered electrode may be a power with a low frequency of 0.5 kHz to 10 kHz, and specifically 0.7 kHz to 5 kHz, but is not limited thereto.

For example, the DBD plasma reactor of the present invention may further include photocatalyst nanoparticles within pores of the macroporous silica that are filled thereinto.

In particular, as the photocatalyst nanoparticle, a transition metal oxide (e.g., $TiO_2$, $ZnO$, $ZrO_2$, $CuO$, $SnO_2$, $V_2O_3$, $CdS$, $WO_3$, and $SrTiO_3$) or a transition metal may be used, but the photocatalyst nanoparticle is not limited thereto. Specifically, among various transition metals or transition metal oxides, materials with a bandgap energy similar to the average electron energy in the DBD plasma may be selected. For example, as the photocatalyst nanoparticle, anatase $TiO_2$, which is known to have the highest activity, may be used, but the photocatalyst nanoparticle is not limited thereto. Additionally, the photocatalyst nanoparticles may be included in an amount of 0.5 wt to 50 wt % based on the weight of the total fillers, but the amount of the photocatalyst nanoparticles is not limited thereto.

As described above, by further including the photocatalyst within pores of the macroporous silica that is filled into the DBD plasma reactor of the present invention, a methane coupling reaction can be performed in which coke formation is reduced or an amount of $C_{5+}$ hydrocarbons being produced is increased compared to a reaction performed by using a reactor in which photocatalyst nanoparticles are not contained under the same reaction conditions.

In a specific embodiment of the present invention, the methane coupling reaction was performed under the same conditions using a reactor, which was constituted by impregnating $TiO_2$ nanoparticles with a size of about 10 nm into the macroporous silica, and another reactor, which had the same constitution except that the $TiO_2$ nanoparticles were not included therein, and the products were compared and analyzed. As a result, it was confirmed that in the case of using a reactor where $TiO_2$ nanoparticles were additionally included, the coke production rate was reduced by about 20%, whereas the amount of $C_{5+}$ hydrocarbons was increased by the corresponding amount (FIG. 13).

Additionally, in the case of using a reactor where a photocatalyst is additionally included within pores of the macroporous silica that is filled into the DBD plasma reactor of the present invention, it is characterized in that the maximum temperature required to remove the formed coke is reduced compared to when a reactor where only photocatalyst nanoparticles are not included is used under the same conditions. This indicates that by using the reactor where the photocatalyst is additionally included, not only can the removal of coke be more easily performed, but also, the amount of coke consumption can be reduced.

Specifically, in a specific embodiment of the present invention, the methane coupling reaction was performed under the same conditions using a reactor, which was constituted by impregnating $TiO_2$ nanoparticles with a size of about 10 nm into the macroporous silica, and another reactor, which had the same constitution except that the $TiO_2$ nanoparticles were not included therein, and the pyrolysis temperature of the coke formed as a result was measured. For example, while increasing the temperature, the changes in mass according to the temperature were measured so as to confirm the temperature at which the coke was decomposed. In particular, the curve showed two peaks, and in the case of using a reactor which was constituted by impregnating $TiO_2$ nanoparticles, the peak position at the higher temperature of the two was formed at a temperature lower by about 20° C. compared to the case of using a reactor not containing the $TiO_2$ nanoparticles (Table 2). This teaches that the coke formed in the corresponding reactor decomposes at a lower temperature; less energy is required to remove the coke; and it is possible to reuse the coke by recycling.

Meanwhile, the present inventors previously proposed a method for removing coke by way of low-temperature plasma under an oxygen atmosphere using a DBD plasma reactor through their previous study (Korean Patent Application No. 10-2018-0128518), and catalysts can be reused by recycling the catalysts by applying the method of coke removal described in the DBD plasma reactor of the present invention.

Advantageous Effects

The present invention can provide a dielectric barrier discharge plasma reactor, which is a reactor for a non-oxidative coupling reaction that is operable at room temperature and ambient pressure, by filling macroporous silica as a dielectric material into the reactor, thereby making it capable of removing the drawbacks of the catalysts in the form of powder (where a pressure difference occurs due to the reaction, etc.), while excluding the inconvenience of pelletization of a catalyst and not causing drawbacks that may occur in a pelletized catalyst. Moreover, the present invention can provide a reactor in which the non-oxidative coupling reaction can be performed such that the amount of coke (a reaction by-product) formed is reduced by additionally including a photocatalyst (e.g., $TiO_2$, etc.) in the macroporous silica. Since the reaction can be performed such that the amount of formation of coke, which is not easily removable and is decomposed at a high temperature, is reduced, the catalyst can be reused by more easily removing the coke from the catalyst.

DETAILED DESCRIPTION OF THE INVENTION

Hereinafter, the present invention will be described in more detail with reference to the following Examples. However, these Examples are for illustrative purposes only, and the scope of the invention is not limited by these Examples.

Preparation Example 1: Synthesis of $TiO_2$/MPS Catalysts

Figure 1:
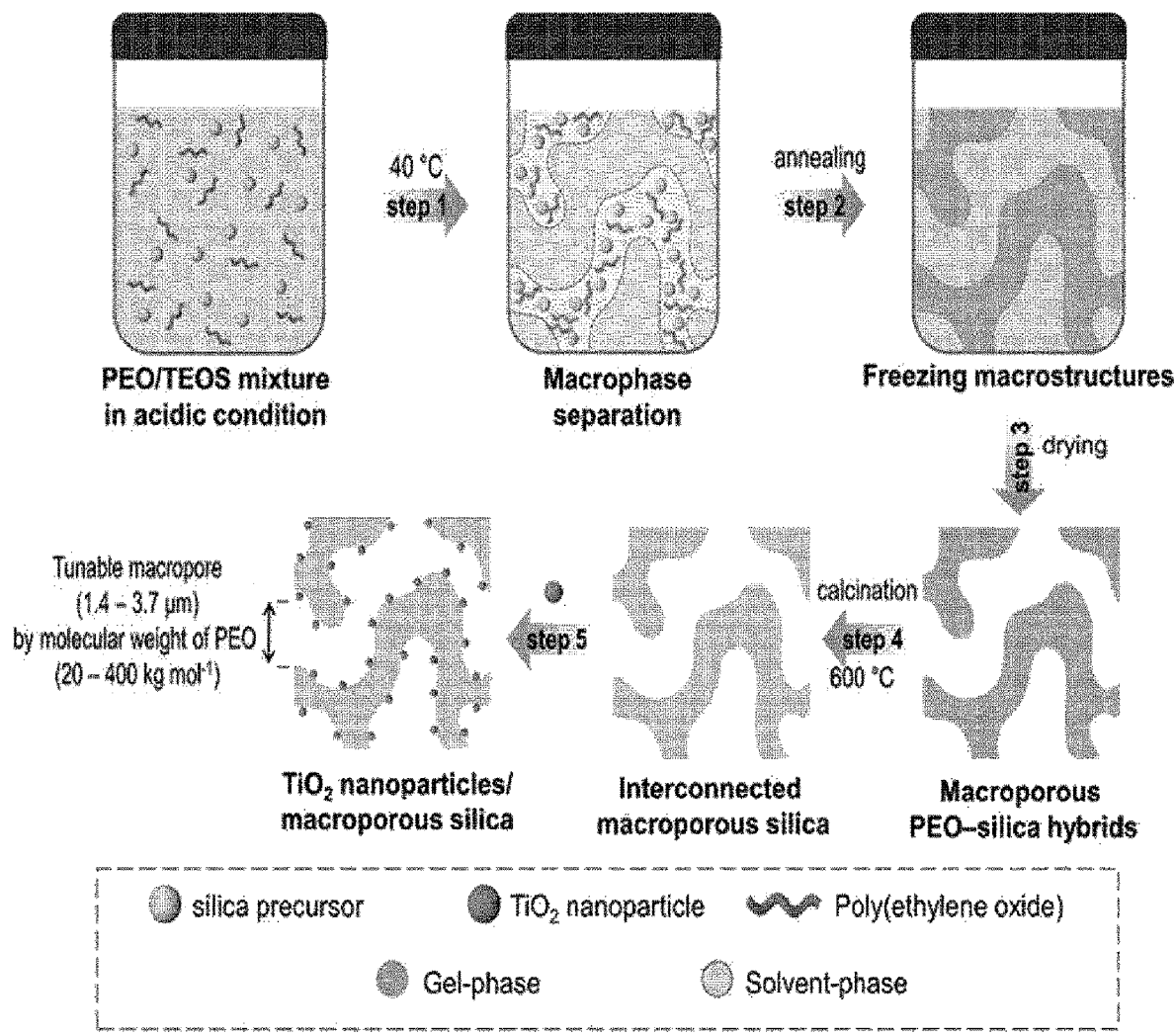
FIG. 1 shows a schematic diagram illustrating a synthesis process of a $TiO_2$ nanoparticle-impregnated macroporous silica catalyst according to an embodiment of the present invention.

Macroporous silica (MPS) was prepared by using macrophase separation via spinodal decomposition and a sol-gel reaction (FIG. 1). Poly(ethylene oxide) (PEO) was used as a phase-separation inducer, and tetraethyl orthosilicate (TEOS) was used as a silica precursor after dissolving it in an acidic aqueous solution. The above homogeneous solution initiated macrophase separation into a gel phase (PEO-silica phase) and a fluid phase (solvent-rich phase) at 40° C. (step 1). The acidic conditions of the solution induced hydrolysis and condensation of TEOS, and thereby silica oligomers were formed by a sol-gel reaction. Since these silica oligomers have a number of silanol groups, PEO could be strongly adsorbed on the silica oligomers by hydrogen bonds between the ether oxygens of PEO and the silanol groups. As the polycondensation of the silica oligomers increased, more silanol sites became available, and thereby PEO-silica complexes were induced. The highly condensed silica oligomers, on which PEO was adsorbed, decreased the mixing entropy and an enthalpic interaction with $H_2O$. As a result, the PEO-silica complexes were thermodynamically less soluble in aqueous solvents. Accordingly, the PEO-silica phase underwent macrophase separation from the solvent-rich phase and induced macro-structured PEO-silica hybrids. An additional annealing process promoted the condensation of the silica oligomers and thereby improved the structural integrity of the macro-structured PEO-silica hybrids (step 2). After washing and drying, macroporous PEO-silica hybrids were obtained (step 3), and three-dimensionally interconnected MPS was formed following calcination at 600° C. in an air-removed PEO species (step 4). In order to provide a $TiO_2$/MPS catalyst, pre-synthesized $TiO_2$ NPs (about 10 nm) were impregnated in the macropores (step 5). The macropore size and the silica framework size were determined by the molecular weight of PEO ($MW_{PEO}$), and accordingly, the size of macropores could be successfully controlled by varying the $MW_{PEO}$.

Specifically, poly(ethylene oxide) (PEO; average $M_n$=20 kg mol$^{-1}$ and 400 kg mol$^{-1}$), tetraethyl orthosilicate (TEOS, 98%), titanium(IV) tetraisopropoxide (TTIP, 97%), and IGEPAL CO-520 were purchased from Sigma-Aldrich. Cyclohexane (99.7%) and ethanol (99.9%) were purchased from Samchun Chemicals. Nitric acid (69%) was purchased from Matsunoen Chemical Ltd.

For the synthesis of macroporous silica (MPS), 8 g of PEO at a concentration of 20 kg mol$^{-1}$ or 400 kg mol$^{-1}$ was uniformly dissolved in 87 g of an aqueous solution of 1.0 M nitric acid under ambient conditions. With vigorous stirring, 65 g of TEOS was added to the mixture and hydrolyzed. After 10 minutes, the solution was gelled in an airtight container and heat-treated at 40° C. for 24 hours (annealed). The thus-obtained macroporous PEO-silica hybrids were washed 5 times with a water-ethanol mixture and dried at 40° C. The dried sample was calcined at 600° C. for 4 hours in air at a heating rate of 1° C./min.

For the synthesis of TiO$_2$ nanoparticles (NPs), 225 mL cyclohexane, 11.5 g of IGEPAL CO-520, 1.25 mL of 0.075 M HCl, and 3 mL of ethanol were mixed to prepare a water-in-oil microemulsion. Thereafter, 0.35 g of TTIP was added to the microemulsion with vigorous stirring at room temperature. After 1 hour, the pre-synthesized TiO$_2$ NPs were washed 3 to 4 times with a 1:1 (v/v) ether/n-hexane mixture to remove the IGEPAL surfactant. Then, the resultant was centrifuged to recover TiO$_2$ NPs and heat-treated at 100° C. for 8 hours. The resultant was calcined at 600° C. for 2 hours in air, and thereby anatase TiO$_2$ NPs were obtained.

In order to prepare NP-impregnated macroporous silica (TiO$_2$/MPS), TiO$_2$ NPs were impregnated into the macropores of MPS using the stirring impregnation method. 1 g of TiO$_2$ NPs was dispersed in 100 mL of ethanol, and then, 20 g of MPS-20 or MPS-400 was added to the mixture. Ethanol was slowly evaporated while stirring the mixture at 50° C. at 150 ppm. TiO$_2$ NP-impregnated MPS was dried in an oven at 50° C. The dried sample was calcined at 500° C. for 5 hours.

Experimental Example 1: Characterization of Prepared Catalysts

The characteristics of MPS and TiO$_2$/MPS samples were analyzed using scanning electron microscopy (SEM, S-4200 field emission SEM, Hitach). The impregnated TiO$_2$ NPs were analyzed by a transmission electron microscope (TEM, Tecnai F20, FEI Company). The powder X-ray diffraction patterns were obtained using a Rigaku D/MAX-2500/PC X-ray diffractometer (Cu K$\alpha$). Nitrogen physisorption analysis was performed for the MPS samples at 77 K using a Tristar II 3020 (Micromeritics Instrument Co.). Fourier-transform infrared spectroscopy (FT-IR) analysis was performed using a Nicolet iS50 spectrometer (Thermo Fisher Scientific, Inc., USA). X-ray photoelectron spectroscopy (XPS) characterization was performed using a VG Scientific Escalab 250 (Al K-alpha X-ray source). The size of macropores was estimated using an AutoPore V (Micromeritics Instrument Co.). The optical spectrum was measured using a UV-Vis spectrometer (Perkin Elmer, Lambda 1050).

After the reaction in the plasma bed, the total mass of the carbonaceous deposits on the spent samples was measured by thermogravimetric analysis (TGA). Specifically, the samples were heated at 100° C. to 800° C. in air at a ramping speed of 20° C./min.

Experimental Example 2: Activity Test

Figure 2:
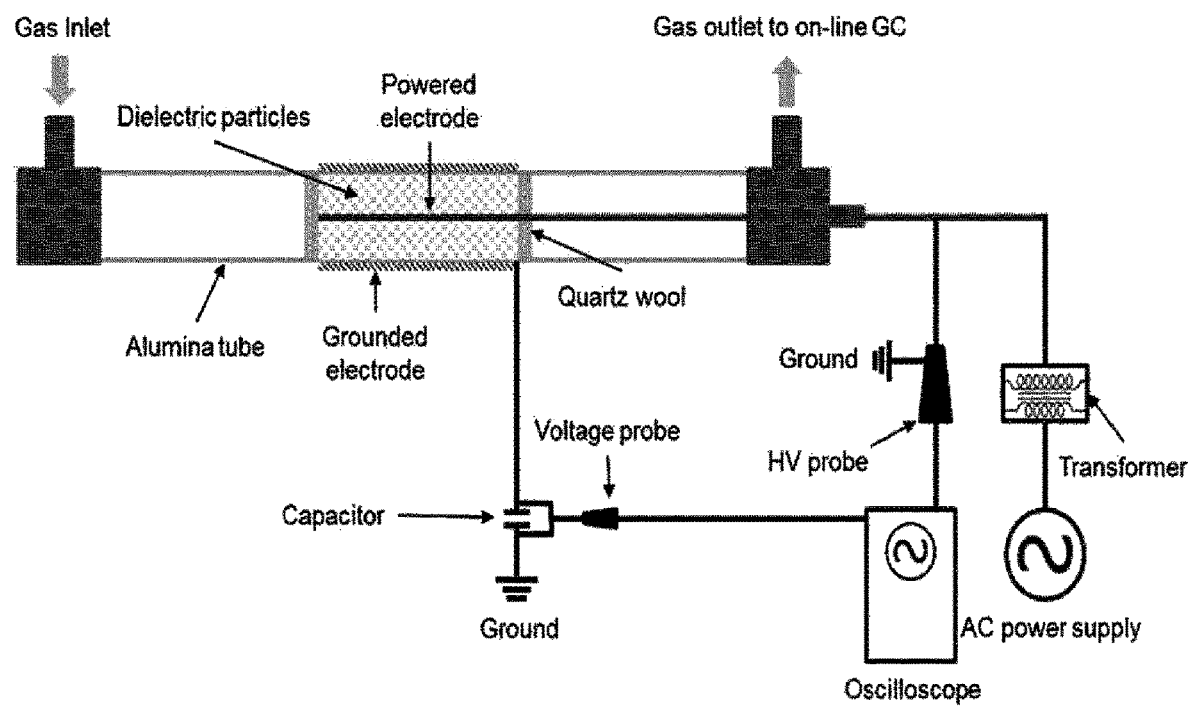
FIG. 2 shows a schematic diagram illustrating a DBD plasma reactor system provided with a packed bed including a macroporous silica catalyst according to an embodiment of the present invention.
Figure 3:
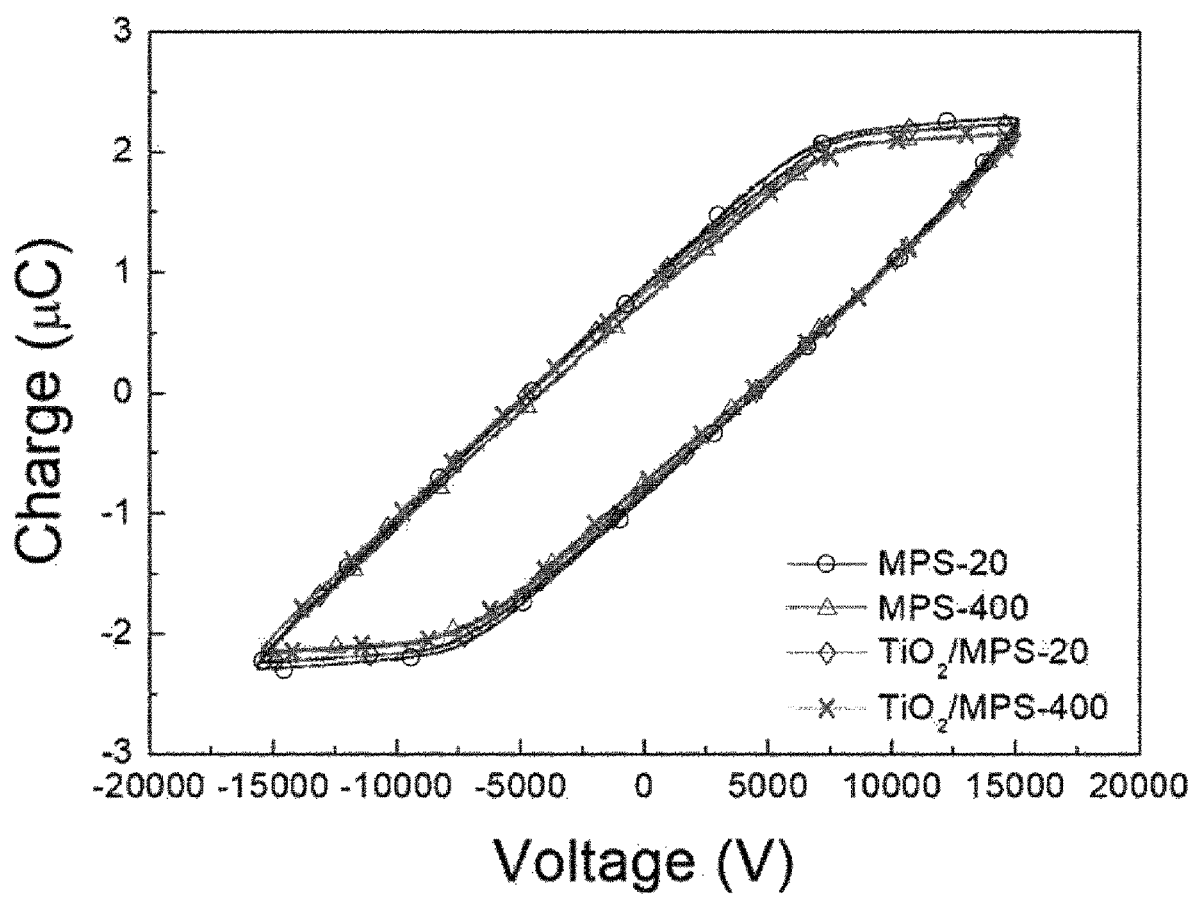
FIG. 3 shows a graph illustrating Q-V Lissajous curves of MPS-20, MPS-400, $TiO_2$/MPS-20, and $TiO_2$/MPS-400.

A non-oxidative plasma-assisted coupling of methane was performed at ambient pressure and room temperature using a packed-bed DBD plasma reactor system prepared in a laboratory. A methane mixture (CH$_4$:N$_2$=1:1) was introduced into the reactor at a volumetric flow rate of 40 sccm (standard cubic centimeter per minute), and the total time required for the entire reaction was 1,000 minutes. FIG. 2 shows a schematic representation of the DBD plasma reactor system used. An alumina tube (inner diameter: 6 mm; thickness: 2 mm) was used as a dielectric barrier for the plasma bed. A stainless steel rod (diameter: 3 mm) was used as a powered electrode and a steel wire was used as a ground electrode. A discharge zone (length: 150 mm) was covered with the ground electrode which was wound around the alumina tube. The discharge gap between the inner surface of the alumina tube and the high-voltage electrode was set to 1.5 mm; the volume of the plasma discharge area was set to 3.181 cm$^3$; and the volume-based space velocity (SV) was set to 754.5 h$^{-1}$. Each dielectric packing material was densely packed in the plasma discharge area (volume: 3.181 cm$^3$). A sinusoidal AC power supply (0 V to 220 V, 60 Hz to 1,000 Hz) was connected to a converter (0 kV to 20 kV, 1,000 Hz). This electric system continuously supplied sinusoidal AC power to the plasma bed. The voltage and frequency applied to the plasma bed were set to 15 kV (30 kV for peak-to-peak voltage) and 1 kHz, respectively. A capacitor with 1 µF of capacitance was connected in series between the plasma bed and the ground. The voltage applied to the plasma bed was measured using a high-voltage probe (1,000:1, P6015A, Tektronix). The voltage across the 1 µF capacitor was measured using a voltage probe (10:1, P6100, Tektronix) connected to each side of the capacitor. The probe was connected to a digital oscilloscope (TDS 3012C, Tektronix), and voltage (V) and charge (Q) Lissajous plots were recorded (FIG. 3). The electric charge accumulated in the plasma bed was calculated by multiplying the voltage across the capacitor by the capacitance of the capacitor (1 µF). Discharge power was calculated by the Lissajous method by using the measured V-Q Lissajous plots disclosed in FIG. 3 and is shown in Table 1.

TABLE 1

| | Breakdown Voltage[a] (kV) | Discharge Power (W) | Weight of Bed (g) | CH$_4$ Consumption in the Bed[b] (µmol · J$^{-1}$ · g$^{-1}$) |
|---|---|---|---|---|
| MPS-20 | 4.53 | 37.9 | 1.55 | 22.8 |
| MPS-400 | 4.16 | 33.1 | 0.821 | 55.8 |
| TiO$_2$/MPS-20 | 4.69 | 37.7 | 1.51 | 26.1 |
| TiO$_2$/MPS-400 | 4.57 | 36.1 | 0.882 | 45.0 |

[a]Measurement from Q-V Lissajous curves (FIG. 3)
[b]CH$_4$ consumption in the bed(µmol · J$^{-1}$ · g$^{-1}$) =

$$\frac{\text{converted CH}_4 \, (\mu\text{mol} \cdot \text{sec}^{-1})}{[\text{Discharge power}(W)] \times [\text{Weight of bed}(g)]}$$

The effluent gas from the plasma bed was analyzed by online gas chromatography (6500GC Young Lin Instrument Co., Korea) by using a Porapak-N and a molecular sieve 13× column connected to a thermal conductivity detector (TCD) and a GS-GasPro column connected to a flame ionization detector (FID). Among the effluent gases, H$_2$, N$_2$, and CH$_4$ were detected by a TCD. Among the effluents, CH$_4$, C$_2$H$_2$, C$_2$H$_4$, C$_2$H$_6$, C$_3$H$_6$, C$_3$H$_8$, 1-C$_4$H$_8$, n-C$_4$H$_{10}$, and unidentifiable C$_5$ to C$_{10}$ hydrocarbons were detected by an FID.

Example 1: Characterization of TiO$_2$/MPS Catalysts

Figure 4:
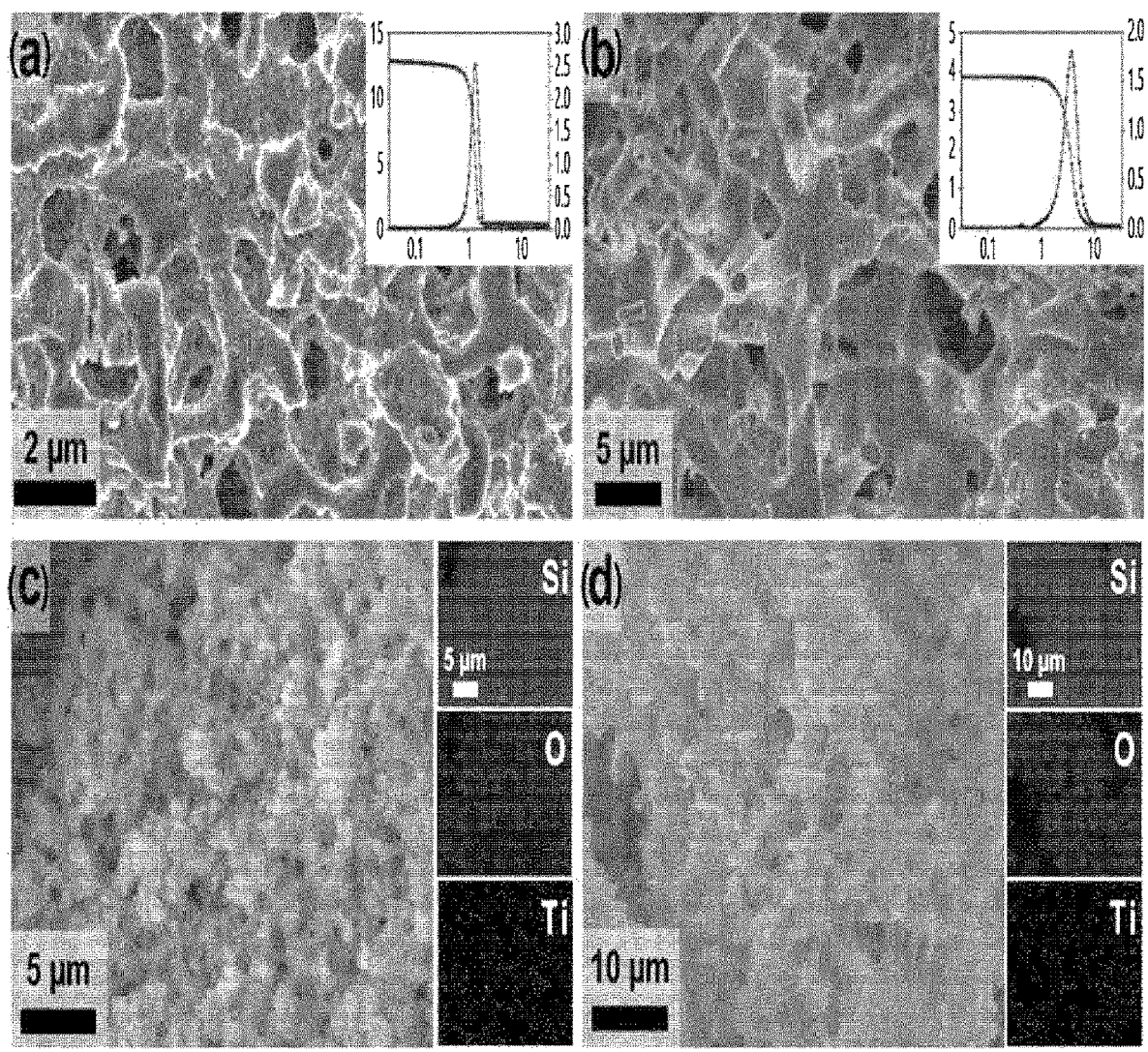
FIG. 4 shows images illustrating the results of microscopic analysis; (a) a SEM image and sizes of corresponding macropores of MPS-20 (inset), (b) a SEM image and a size of corresponding macropores of MPS-400 (inset), (c) a SEM image and EDS mapping in Si, 0, and Ti of $TiO_2$/MPS-20, and (d) a SEM image and EDS mapping in Si, 0, and Ti of $TiO_2$/MPS-400.
Figure 5:
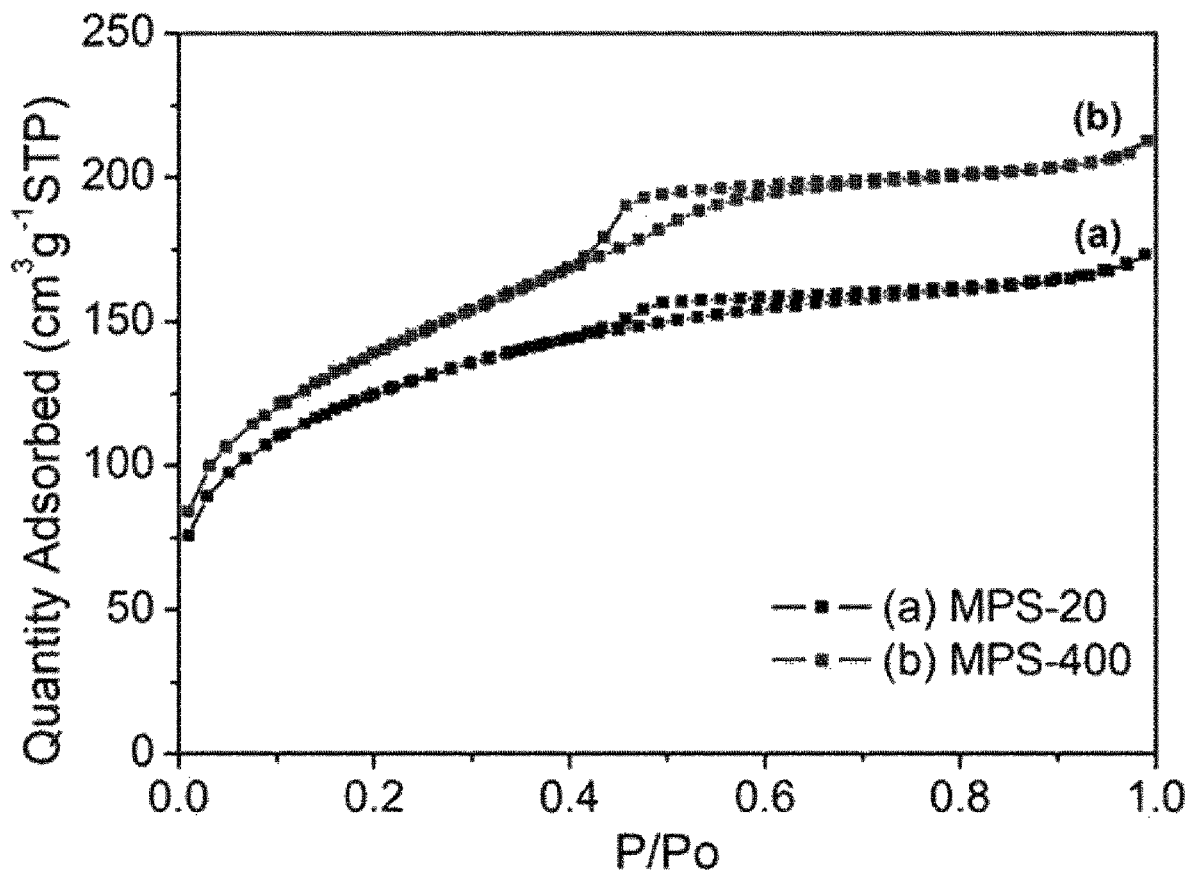
FIG. 5 shows a graph illustrating adsorption-desorption isotherms of (a) MPS-20 and (b) MPS-400.

In order to confirm the effects of the pore size of the macroporous silica prepared according to the Preparation Examples above, two types of MPS with different macropores sizes of 1.4 µm and 3.7 µm were prepared by using PEO of 20 kg mol$^{-1}$ and 400 kg mol$^{-1}$, respectively. Each sample was indicated as MPS-(MW$_{PEO}$). SEM images showed that both MPS samples have a 3D network shape, in which bicontinuous silica frameworks and interconnected macropores co-exist (FIGS. 4a and 4b). When PEO of 20 kg mol$^{-1}$ was used, a well-developed macropore structure was observed over the entire framework (FIG. 4a). The size of the macropores calculated by a mercury porosimeter was 1.4 µm, which corresponded to the SEM image (inset of FIG. 4a). The Brunauer-Emmett-Teller (BET) surface area of MPS-20 analyzed by nitrogen adsorption-desorption was 414 m$^2$ g$^{-1}$ (FIG. 5). As MW$_{PEO}$ increases, a higher MW$_{PEO}$ increases the local concentration of PEO during the macrophase separation process, and this is advantageous in stabilizing more silica oligomers. Such behavior increases the size of the macroscale-separated domains. When the MW$_{PEO}$ was 400 kg mol$^{-1}$, the size of the bicontinuous silica domain of MPS-400 was larger than that of MPS-20 (FIG. 4b). In addition, the size of the macropores was increased up to 3.7 µm, and the BET surface area corresponded to 481 m$^2$ g$^{-1}$ (inset of FIG. 4b and FIG. 5).

Figure 6:
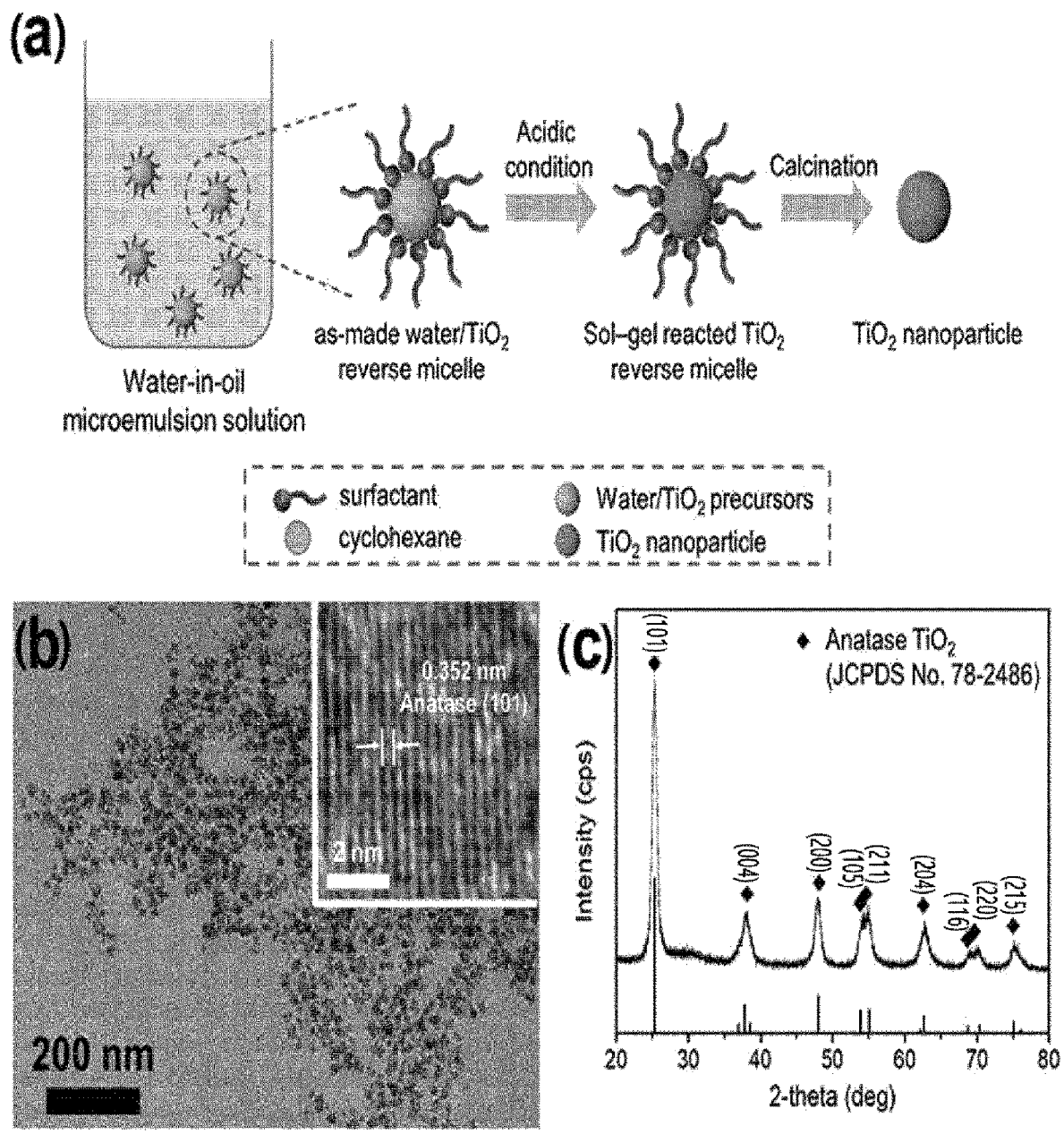
FIG. 6 shows a schematic diagram illustrating (a) the synthesis of $TiO_2$ nanoparticles (NPs) by water-in-oil microemulsion, (b) a TEM image and a crystalline phase of $TiO_2$ NPs (inset), and (c) an XRD pattern of $TiO_2$ NPs.
Figure 7:
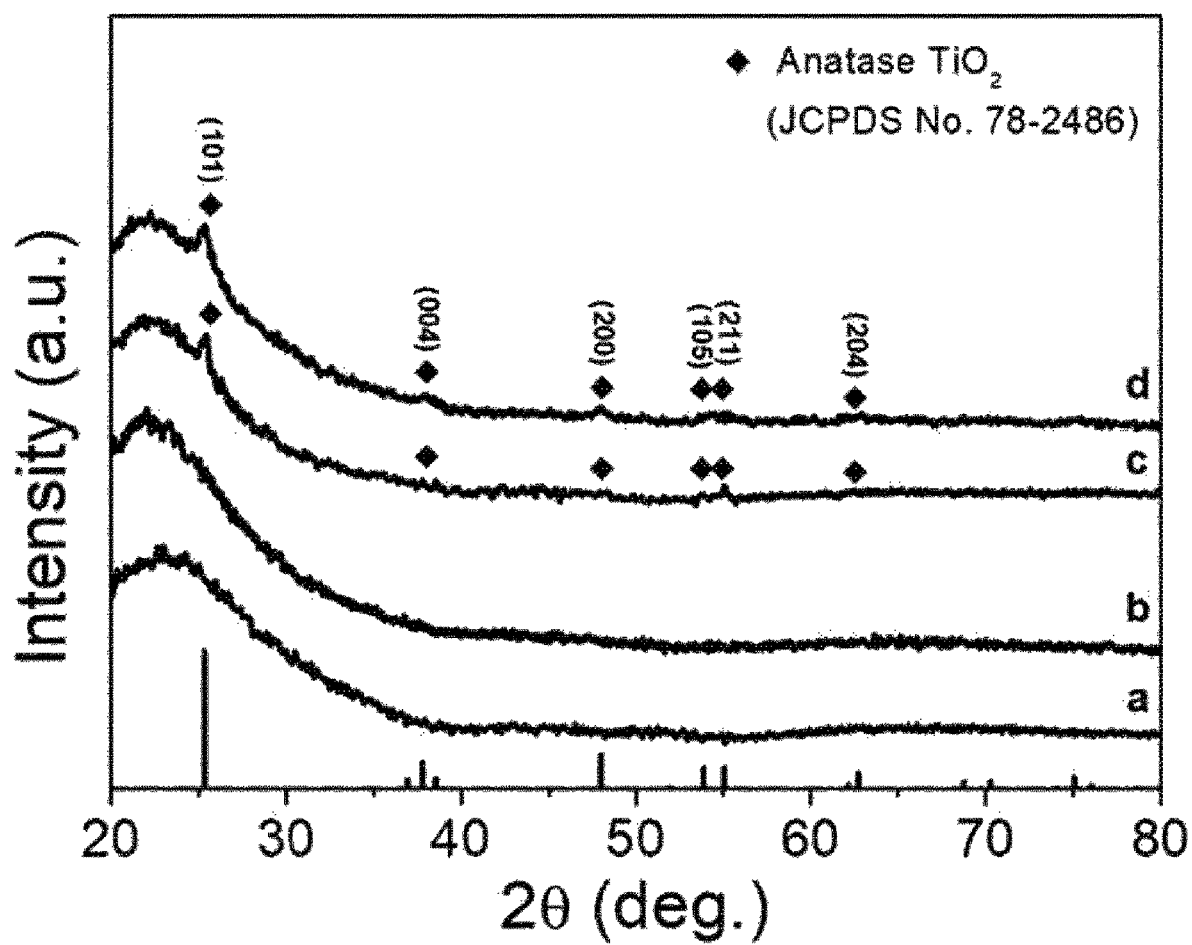
FIG. 7 shows a graph illustrating XRD patterns of (a) MPS-20, (b) MPS-400, (c) $TiO_2$/MPS-20, and (d) $TiO_2$/MPS-400.
Figure 8:
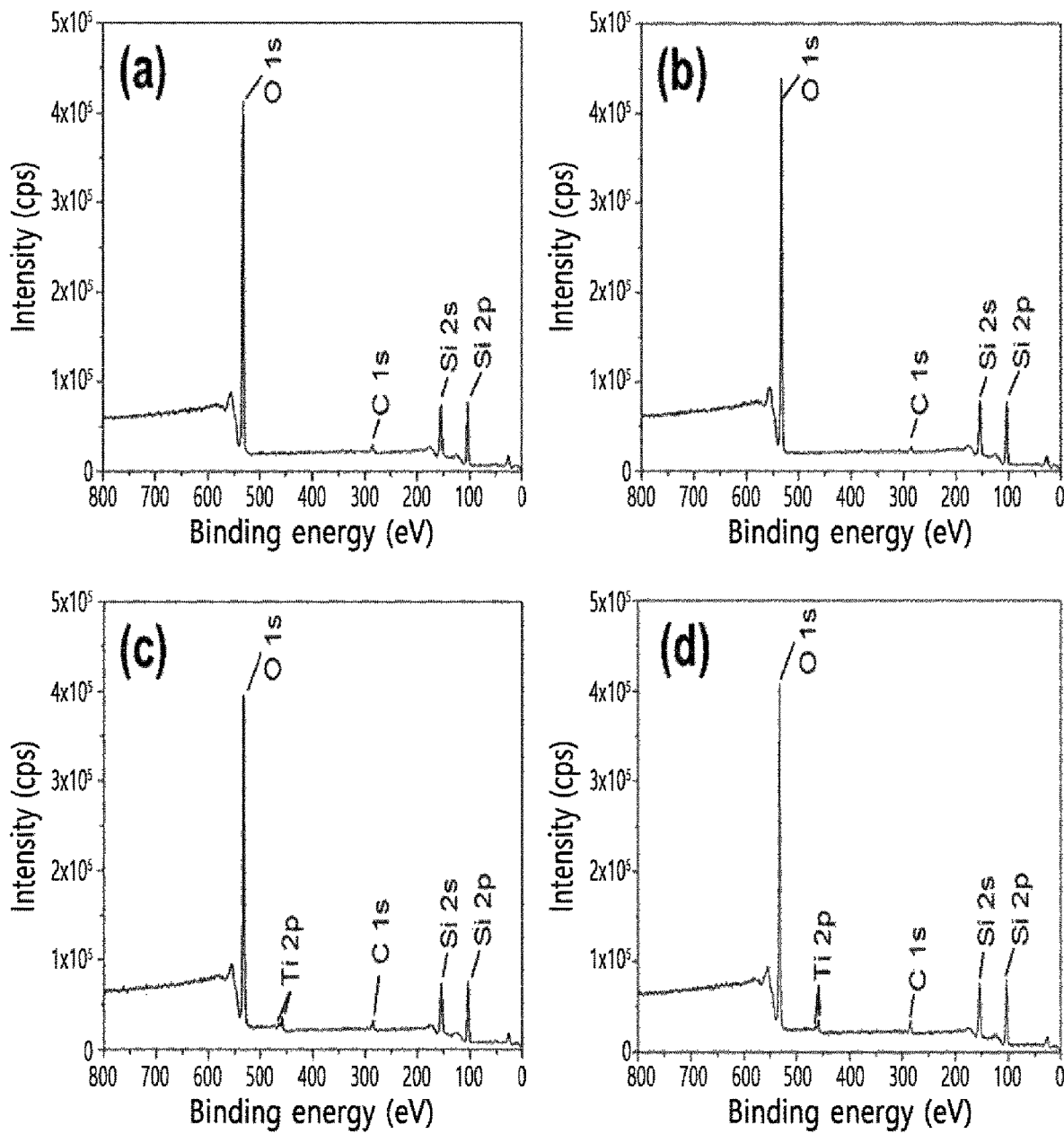
FIG. 8 shows the results of XPS survey spectra of (a) fresh MPS-20 and (b) fresh MPS-400; and XPS survey spectra of (c) fresh $TiO_2$/MPS-20 and (d) fresh $TiO_2$/MPS-400.

TiO$_2$ NPs were prepared by a water-in-oil-type microemulsion method which uses cyclohexane, an acidic ethanol-water mixture, IGEPAL CO-520 as a surfactant, and TTIP as a TiO$_2$ precursor (FIG. 6a). Surfactant molecules form reverse micelles by stabilizing the acidic aqueous mixture in cyclohexane. The acidic conditions inside the microemulsion induced a sol-gel reaction of TTIP, and thereby as-made TiO$_2$ NPs were provided. By calcining at 600° C. in air, highly crystalline TiO$_2$ NPs were obtained without aggregation between nanoparticles (FIG. 6b). The high-resolution transmission electron microscopy (HRTEM) image shows a crystalline phase of anatase TiO$_2$ (101) with a spacing of 0.352 nm (inset of FIG. 6b). The XRD pattern of the TiO$_2$ NPs was consistent with the anatase TiO$_2$ peaks (JCPDS No. 78-2486), and the average size of the crystallites calculated through the Debye-Scherrer equation was about 10 nm (FIG. 6c). The energy dispersive spectrometry (EDS) mapping indicates that TiO$_2$ NPs were evenly distributed within the MPS framework (FIGS. 4c and 4d). The XRD patterns of TiO$_2$/MPS-20 and TiO$_2$/MPS-400 showed anatase TiO$_2$ peaks with broad amorphous silica peaks, and this demonstrates the presence of TiO$_2$ NPs in both MPS (FIG. 7). The average size of crystallites of the impregnated TiO$_2$ NPs was calculated by the Debye-Scherrer equation. The size of the TiO$_2$ crystallites of TiO$_2$/MPS-20 and TiO$_2$/MPS-400 determined at 2θ=25.4° from the XRD spectra (FIG. 7) were 4.86 wt % and 4.79 wt %, respectively. These values were determined by XPS analysis (FIG. 8).

Figure 9:
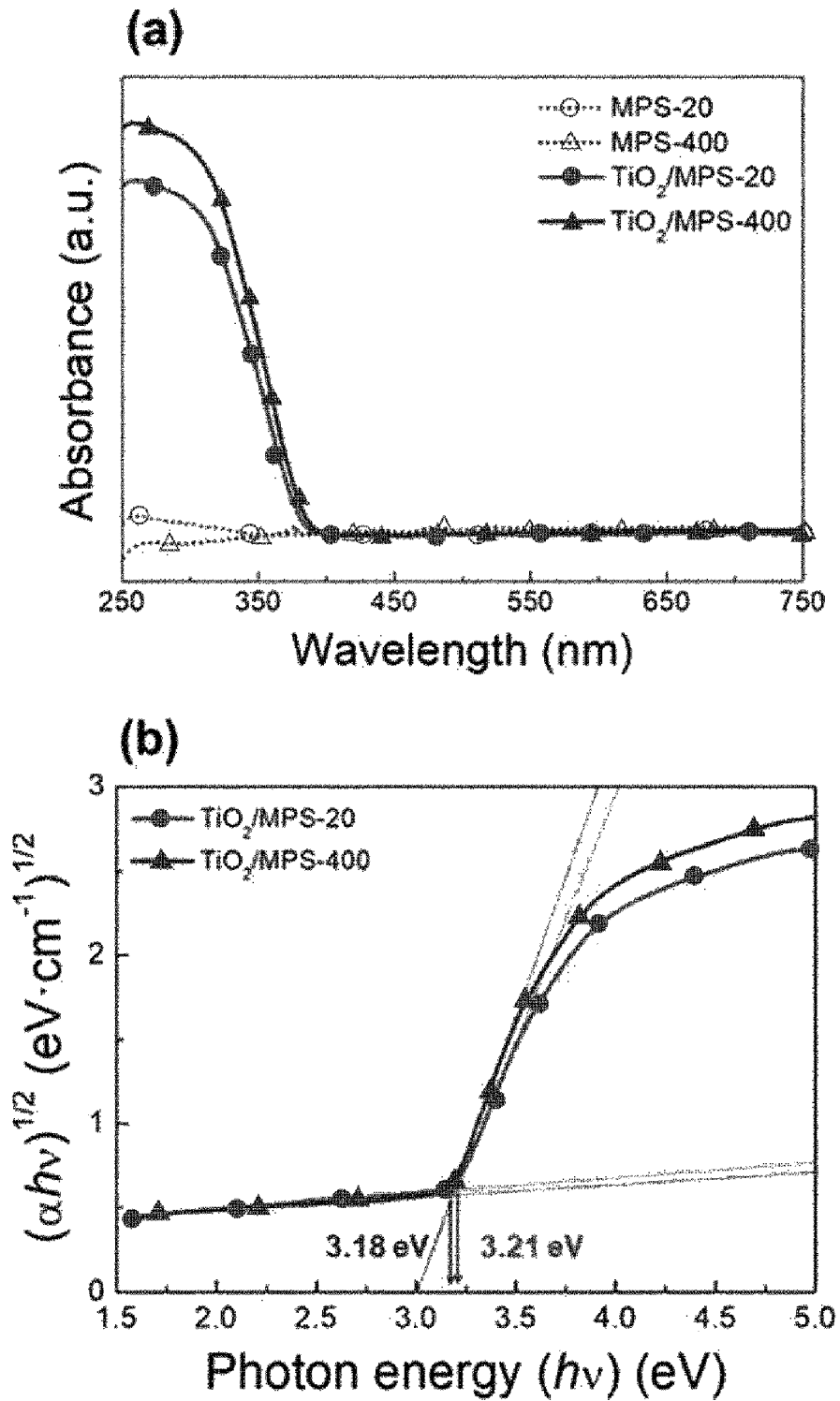
FIG. 9 shows the results of (a) UV-Vis spectra of MPS-20, MPS-400, $TiO_2$/MPS-20, and $TiO_2$/MPS-400; and (b) Tauc plots of $TiO_2$/MPS-20 and $TiO_2$/MPS-400.
Figure 10:
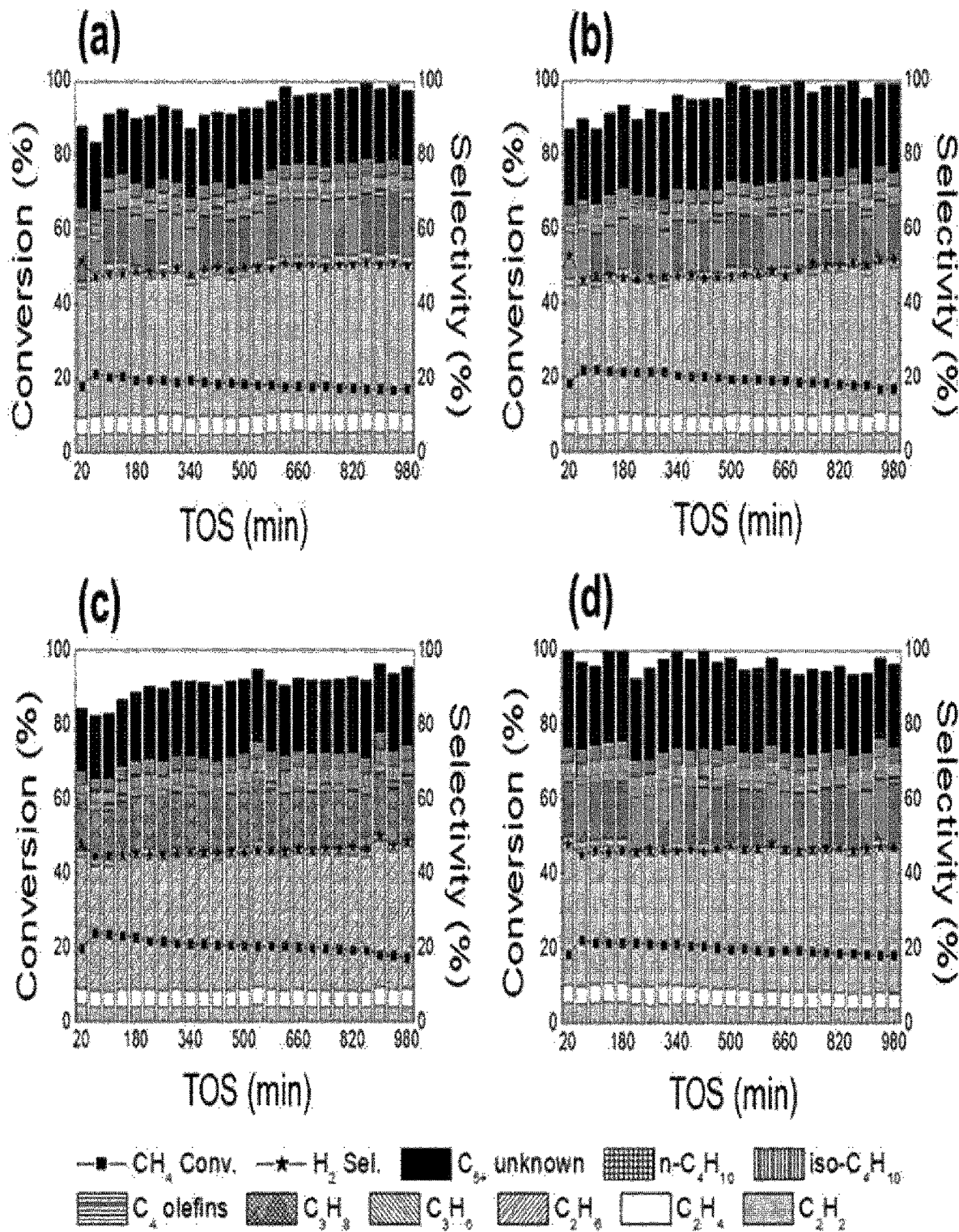
FIG. 10 shows the results of reaction performances of (a) MPS-20, (b) $TiO_2$/MPS-20, (c) MPS-400, and (d) $TiO_2$/MPS-400 as a function of time on stream (TOS), in $CH_4$ conversion rate and product selectivity.

FIG. 9a shows UV-Vis spectra of freshly prepared samples. In the spectra, UV absorption below 396 nm was shown to be increased significantly in the spectra of TiO$_2$/MPS-20 and TiO$_2$/MPS-400. It is known that N$_2$ and CH$_4$ discharges in the DBD plasma bed can be a weak light source of UV rays, and in the DBD plasma discharge, electrons have an average energy of 3 eV to 4 eV, which is close to the bandgap energy of 3.2 eV. Such known values of bandgap energy appeared to be in good agreement with those which were observed in the present invention by the Tauc plots from the UV-Vis spectrum (FIG. 9b). After strict baseline correction, the bandgap energy values were determined to be 3.21 eV and 3.18 eV for TiO$_2$/MPS-20 and TiO$_2$/MPS-400, respectively. Therefore, the impregnated TiO$_2$ was expected to be directly activated by the DBD plasma.

Example 2: Performance with Respect to Methane Coupling Reaction

Figure 11:
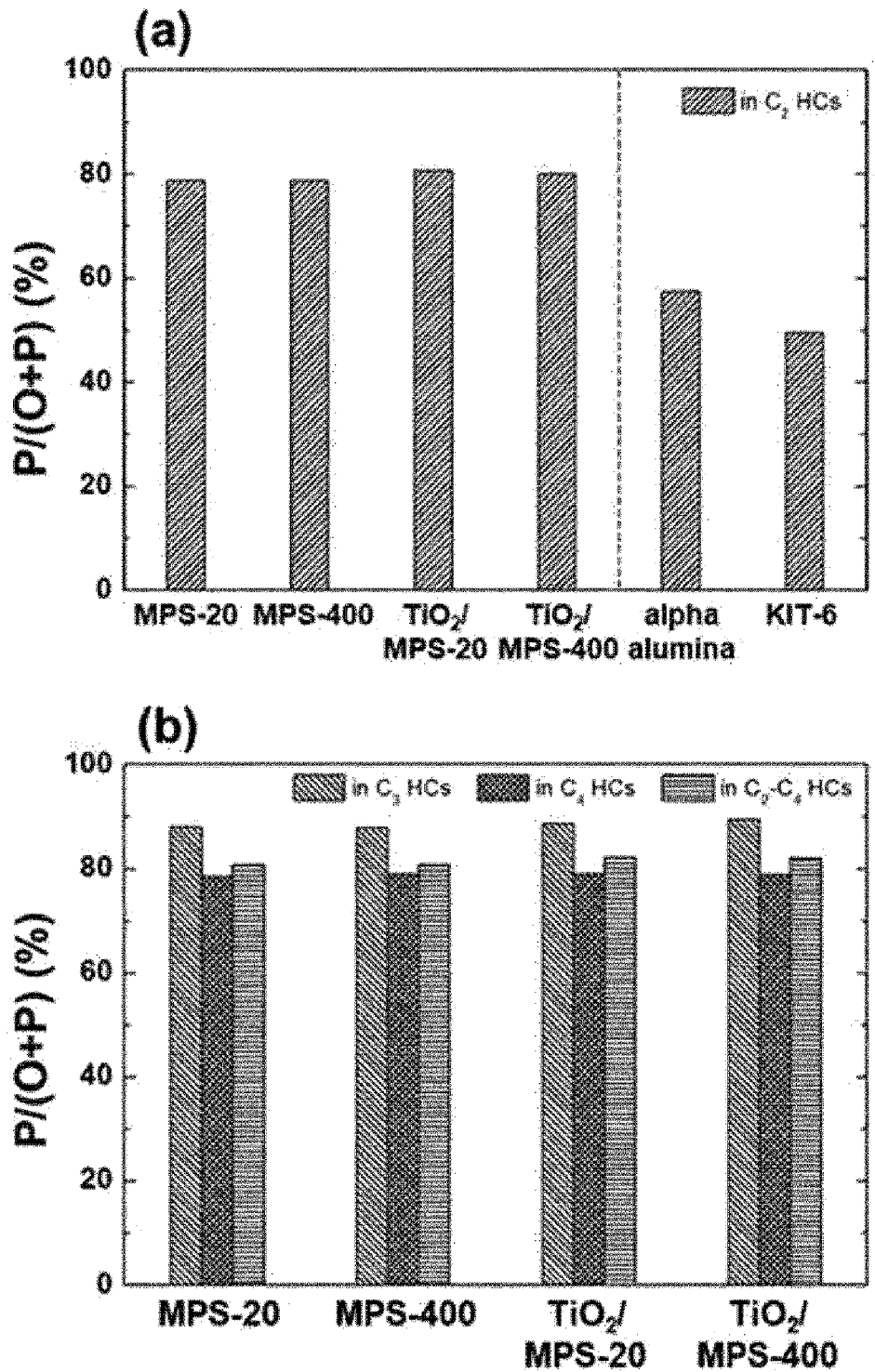
FIG. 11 shows a graph illustrating (a) paraffin fractions in $C_2$ hydrocarbons, which are produced by using MPS-20, $TiO_2$/MPS-20, MPS-400, $TiO_2$/MPS-400, alpha alumina (from Chem. Eng. J., 377 (2019) 119896), and KIT-6 (from Chem. Eng. J., 377 (2019) 119896) as a catalyst; and a graph illustrating (b) paraffin fractions in $C_3$, $C_4$, and $C_2$ to $C_4$ hydrocarbons produced by using MPS-20, $TiO_2$/MPS-20, MPS-400, and $TiO_2$/MPS-400 as a catalyst.

FIGS. 10a to 10d show the results of the methane coupling reaction of each sample under the same plasma conditions. In all of the cases, the performances of all of the samples were shown to be very similar to each other in CH$_4$ conversion rate and selectivity of C$_2$ to C$_4$ hydrocarbon species. The CH$_4$ conversion rate was shown to be almost 20% in all of the cases. The selectivity of C$_2$, C$_3$, and C$_4$ hydrocarbons was almost 50%, 15%, and 10%, respectively. However, it was found that the paraffin fraction of light hydrocarbons was remarkably increased compared to the results of very fine powder samples. FIG. 11a shows the paraffin fraction of C$_2$ hydrocarbons. From the beginning, the four results are for MPS powder samples, and the paraffin fraction of these samples ranged from 78.8% to 80.7% in the C$_2$ hydrocarbons. For comparison, two experimental results (Chem. Eng. J., 377 (2019), 119896) of fine dielectric material powder from previous studies by the present inventors are shown together on the right. The above samples were mesoporous alpha alumina with a relatively small BET area and highly aligned mesoporous KIT-6 silica with a very large BET area. By comparing these results, it was found that the paraffin fraction in the present invention was remarkably higher compared to that in the very fine powder. According to the previous studies of the present inventors, the gap distance between the particles of the polarized dielectric material, which is proportional to their particle size, had a significant effect on the reaction performance. The smaller gap distance provided a denser environment of the reactant molecules, and accordingly, more collisions between radicals as well as dehydrogenation were induced. FIG. 11b shows the paraffin fraction of C$_3$, C$_4$, and C$_2$ to C$_4$ hydrocarbons in the MPS powder samples. The paraffin fraction of these samples was about 80% in the range of light hydrocarbons. The above results were shown to be very similar to those of pelletized dielectric materials in other literature (Fuel, 90 (2011) 1946-1952; and Plasma Chem. Plasma Process., 23 (2003) 283-296). These results suggest that the disadvantages in the pelletizing process, such as limitations on mass transfer and modification of physical and chemical properties of the base material, may be prevented by using these macroporous powder samples in the plasma bed.

In order to further confirm the effects of the size of macropores on performance, the converted amounts of CH$_4$ per unit power and unit bed weight are shown (Table 1). Table 1 shows that a much higher amount of light hydrocarbons can be obtained when a dielectric material with the same power and weight is used. In other words, when macroporous silica with a larger pore size is used, a much smaller amount of a dielectric material is required to obtain the same amount of the product under the same reaction conditions including plasma irradiation. In each case, the discharge power in the plasma bed was calculated using the corresponding Lissajous curve disclosed in FIG. 3.

Example 3: Analysis after Plasma Reaction

Figure 12:
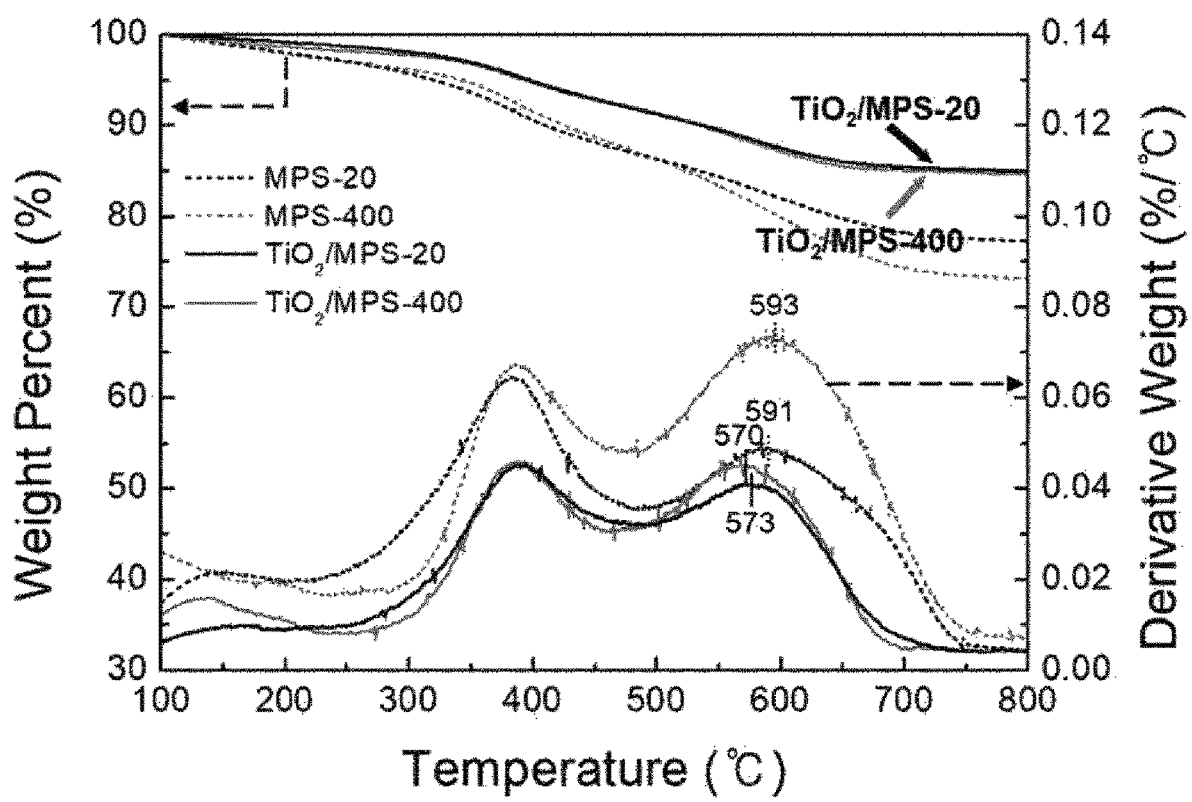
FIG. 12 shows a graph illustrating the TG/DTA results of the spent MPS-20, MPS-400, $TiO_2$/MPS-20, and $TiO_2$/MPS-400.

FIG. 12 and Table 2 show the TG/DTA results for all of the spent samples. From the TGA results, it was found that the amount of coke was significantly reduced in the case of the consumed TiO$_2$/MPS samples. From the DTA results, two kinds of coke were observed. The temperature of the lower DTA peak was very similar in all of the cases. However, in the case of all of the spent TiO$_2$/MPS samples, the temperature of the higher DTA peak was shifted to a temperature that is lowered by about 20° C. compared to the results for the spent MPS samples. The above shift to the lower temperature indicates that impregnated TiO$_2$ NPs increase the resistance to coke deposition and that the deposited coke is converted to a more easily removable type.

TABLE 2

| Sample | Weight Loss (%) | Temperature of Lower DTA Peak (° C.) | Temperature of Higher DTA Peak (° C.) |
| --- | --- | --- | --- |
| MPS-20 | 23.0 | 384 | 591 |
| MPS-400 | 27.2 | 386 | 593 |
| TiO$_2$/MPS-20 | 15.2 | 390 | 573 |
| TiO$_2$/MPS-400 | 15.5 | 389 | 570 |

Figure 13:
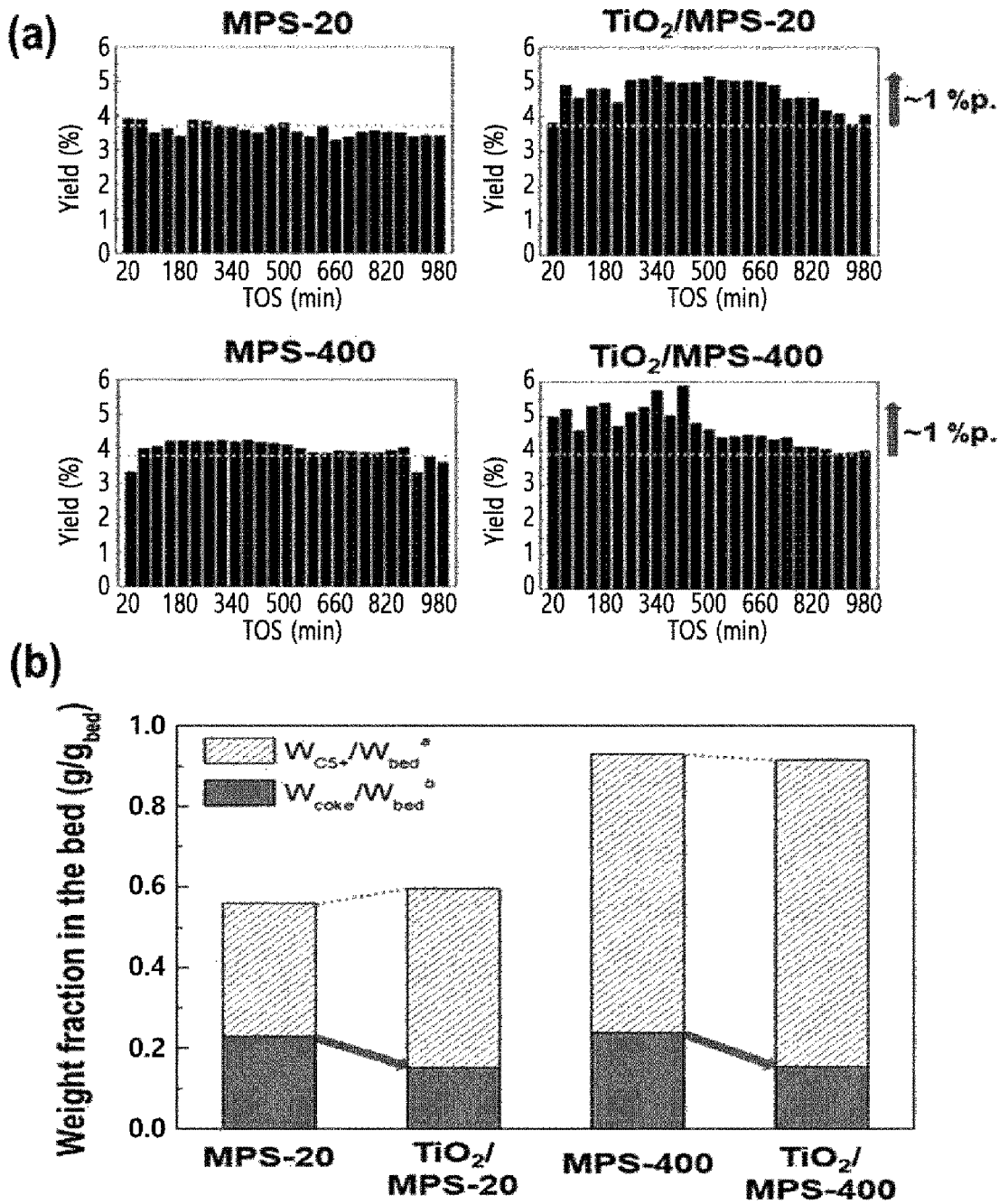
FIG. 13 shows (a) results illustrating the yields of $C_{5+}$ hydrocarbon products of a sample as a function of TOS and (b) a graph illustrating the cumulative weight of hydrocarbon products, which is calculated by dividing into the weight of coke (and by the weight of bed in the cases of MPS-20, $TiO_2$/MPS-20, MPS-400, and $TiO_2$/MPS-400).

For further explanation of the TG/DTA results, the yield of long-chain (C$_{5+}$) hydrocarbons detected by online GC was investigated. Due to the limitations of the GC measurement, not all of the C$_{5+}$ hydrocarbons were included. The materials contained in the C$_{5+}$ hydrocarbons were shown to be isomers of paraffins and olefins of C$_5$ to C$_{10}$ hydrocarbons. In FIG. 13a, the yield of the C$_{5+}$ hydrocarbons of the TiO$_2$/MPS samples was significantly higher than that of the MPS samples. To compare with the TG/DTA results, the cumulative weight and coke mass of the C$_{5+}$ products, divided by the mass of the plasma bed, were calculated and compared in FIG. 13b. In the case of the TiO$_2$/MPS samples, a significant fraction was converted to the C$_{5+}$ products, otherwise they were eventually converted to coke. Comparing the increase in the amount of C$_{5+}$ products and the decrease in the amount of coke, the two amounts were similar.

Under plasma discharge conditions, oxygen vacancies could be generated on the surface of TiO$_2$ by the bombardment of electrons having an accelerated energy and by plasma-radiated UV. An et al. reported the effects of H$_2$ plasma treatment on nanoporous TiO$_2$ photocatalysts (*Sci. Rep.*, 6 (2016) 29683). From the above, it was concluded that the improved photocatalyst activity of H$_2$ plasma-treated TiO$_2$ is due to the formation of oxygen vacancies on the surface of TiO$_2$ during the H$_2$ plasma treatment process, and that the generation of oxygen vacancies was confirmed by an XPS survey. The experiment of the present invention was performed under non-oxidative conditions, and hydrogen molecules were sufficiently generated during the plasma-induced coupling process of methane molecules (asterisk-marked lines in FIGS. 10a to 10d; averaged H$_2$ selectivity in all experiments was between 46.1% and 49.6%). The hydrogen molecules generated in abundance and non-oxidative conditions established reductive conditions, and the TiO$_2$ NPs were reduced (i.e., reduction of Ti$^{4+}$ to Ti$^{3+}$), and surface oxygen vacancies were generated. A detailed discussion on the generation of reduced Ti ionic species will be covered in the XPS section.

Figure 14:
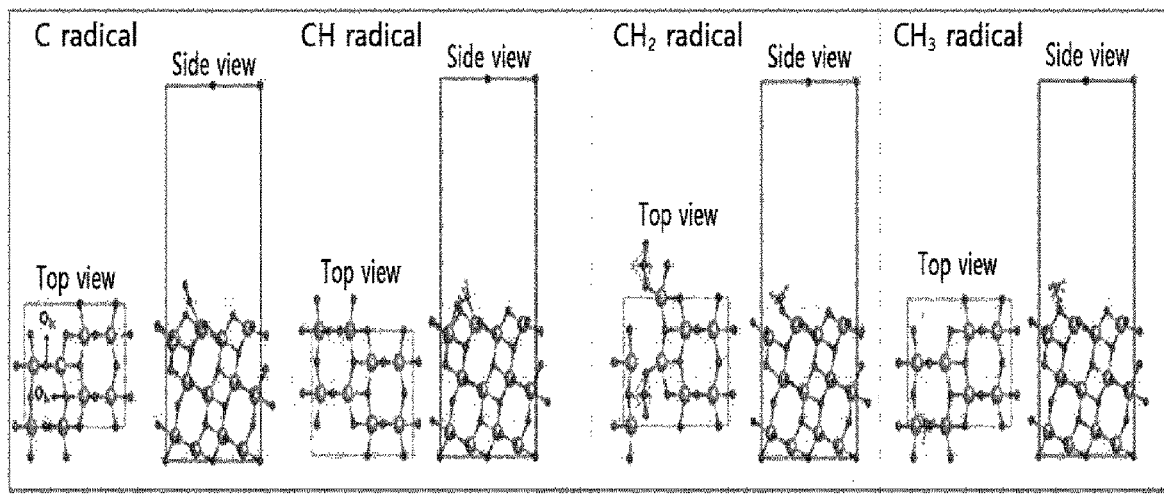
FIG. 14 shows drawings, in which (a) represents the calculated most stable adsorption site on the $TiO_2$ (101) surface with respect to adsorption of $CH_x$ (x=0 to 3) radicals species, (b) represents the calculated dehydrogenation energy of $CH_x$ (x=0 to 3) radicals which are adsorbed on the anatase $TiO_2$ (101) surface, and (c) represents the calculated relative stability of $CH_x$ (x=0 to 3) radicals which are adsorbed on the anatase $TiO_2$ (101) surface, using the DFT (density functional theory) method. Midium filled circles, large open circles, small filled circles, and tiny dots represent oxygen, titanium, carbon, and hydrogen atoms, respectively.
Figure 14:
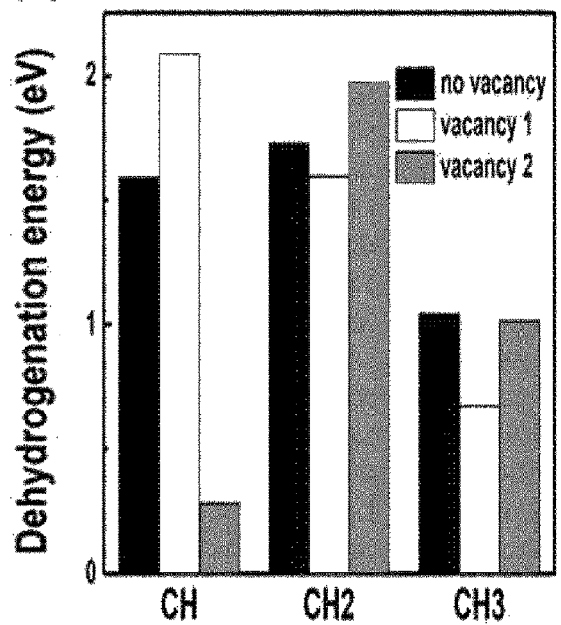
Figure 14:
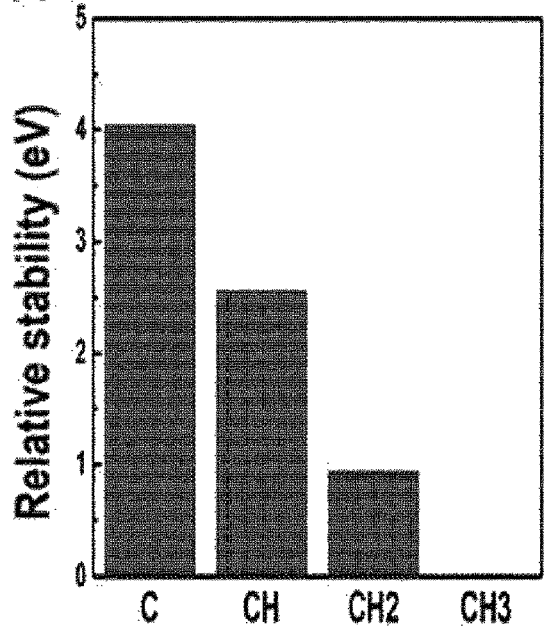

Huygh et al. reported the DFT calculation results of adsorption energy of CH$_x$ (x=0 to 3) radical species on oxygen vacancies of the surface and subsurface of the TiO$_2$ lattices (*J. Phys. Chem. C*, 119 (2015) 4908-4921). According to the above calculation results, while CH$_2$ and CH$_3$ radical species were preferentially adsorbed to the surface oxygen vacancies formed on the (001) facets of TiO$_2$, CH and C radical species were hardly adsorbed to the surface oxygen vacancies. With respect to the subsurface oxygen vacancies formed on the (001) facets of TiO$_2$, it was reported that subsurface oxygen vacancies are preferentially adsorbed by CH$_3$ radicals compared to CH$_2$, CH, and C radicals. Additionally, the dehydrogenation energy and relative stability on the (101) surface of anatase TiO$_2$, to which CH$_x$ radicals were adsorbed, were calculated using DFT (FIGS. 14a to 14c). Before the above step, Huygh et al. compared the coking resistance of the (001) facets of anatase TiO$_2$, which contains a nickel-based catalyst, by using the dehydrogenation energy of CH$_x$ radicals on the surface of the catalyst (*J. Catal.*, 311 (2014) 469-480; *J. Phys. Chem. C*, 122 (2018) 9389-9396). Huygh et al. explained the positive dehydrogenation energy as a source of the high coking resistance of TiO$_2$. Additionally, in order to confirm the generality of coking resistance of anatase TiO$_2$, similar calculations were performed on the (101) surface of anatase TiO$_2$, which is the most stable surface of anatase TiO$_2$ (XRD patterns of FIGS. 7 and 6c). The specific DFT calculation method is shown in Experimental Example 3 below. As shown in FIG. 14b, the CH$_x$ radical adsorbed on the (101) surface has a positive dehydrogenation energy regardless of the formation of oxygen vacancies. Additionally, as reported for the (001) facet by Huygh et al. (FIG. 14c), CH$_3$ and CH$_2$ radicals have higher relative stability than CH and C radicals on the (101) surface. In conclusion, it was confirmed that anatase TiO$_2$ had coking resistance regardless of the formation of facets and oxygen vacancies.

The present inventors confirmed the microdischarge by particles of a dielectric material through their previous studies (*Chem. Eng. J.*, 377 (2019) 119896). In a plasma environment, there are sheath layers near anode and cathode electrodes where the electron density decreases exponentially due to boundary condition. Since TiO$_2$ nanoparticles located on the polarized microelectrode exist under the sheath layer, adsorbed radicals are protected from high-energy electrons and have high coking resistance due to TiO$_2$ nanoparticles.

According to the reaction pathway proposed in the previous research of the present inventors, CH and C radical species are considered as a coke precursor in the non-oxidative coupling of methane in a DBD plasma generator. With respect to TiO$_2$/MPS samples, coke precursors (e.g., C and CH radical species) were not shown to adsorb favorably to the generated surface of TiO$_2$ NPs. With respect to the C and CH radical species, which were adsorbed to the surface of TiO$_2$ NPs, further dehydrogenation to carbon deposits was shown to be significantly inhibited. Therefore, more opportunities were given to bind and hydrogenate with C$_x$H$_y$ and H radicals than for C and CH radical species to be adsorbed on the surface and converted to carbon deposits. In the cases of TiO$_2$/MPS samples, while these effects were shown to induce increased yields of C$_{5+}$ hydrocarbon products (FIG. 13a), a lesser amount of carbon deposits was observed in the TG/DTA results compared to the cases of the MPS samples (FIG. 12).

In addition, when oxygen vacancies were generated, lattice oxygen atoms could be released from the surface of TiO$_2$ NPs. According to the reaction pathway proposed in the previous studies of the present inventors, hydrogen radicals (H·) were generated during the plasma-induced coupling process of methane and participated in the plasma reaction. In plasma, hydrogen radicals (H·) were shown to react with surface lattice oxygen as well as lattice oxygen released and thereby induce the formation of hydroxyl radicals (OH·). Hydroxyl radicals are known as major components for decomposition of organic compounds on a TiO$_2$ catalyst. From the experimental results of the present invention, hydroxyl radicals derived from lattice oxygen were shown to attack tar-like heavy hydrocarbons. A greater amount of hydroxyl radicals was produced more in the case of TiO$_2$/MPS samples, and as a result, a greater amount of C$_5$ to C$_{10}$ hydrocarbons was produced in the case of TiO$_2$/MPS samples.

Figure 15:
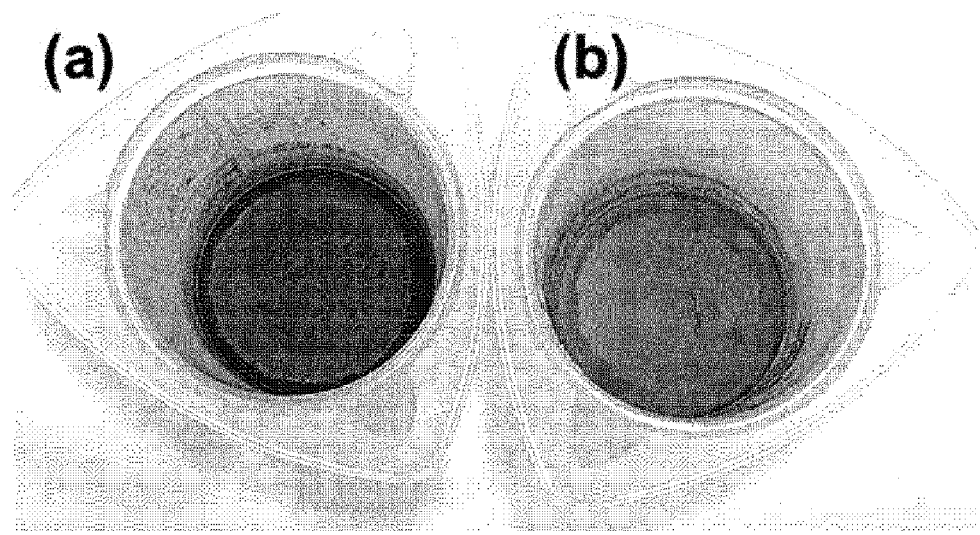
FIG. 15 shows images illustrating a tar-like material obtained from (a) a spent MPS-400 bed and (b) a spent $TiO_2$/MPS-400 bed.

FIG. 15 shows images of tar-like carbonaceous deposits recovered from a spent MPS-400 bed and a spent TiO$_2$/MPS-400 bed (FIG. 15a and FIG. 15b, respectively). The color of the carbonaceous deposit of the spent TiO$_2$/MPS-400 bed (FIG. 15b) was much brighter than that of the spent MPS-400 bed (FIG. 15a). Such a result directly indicates that the deposition of a tar-like or coke-like material is significantly inhibited when TiO$_2$ NPs are used in a plasma bed, and this result was consistent with the results of TG/DTA, where the amount of carbon deposit was significantly reduced and the peak at a higher temperature shifted to a lower side.

Figure 16:
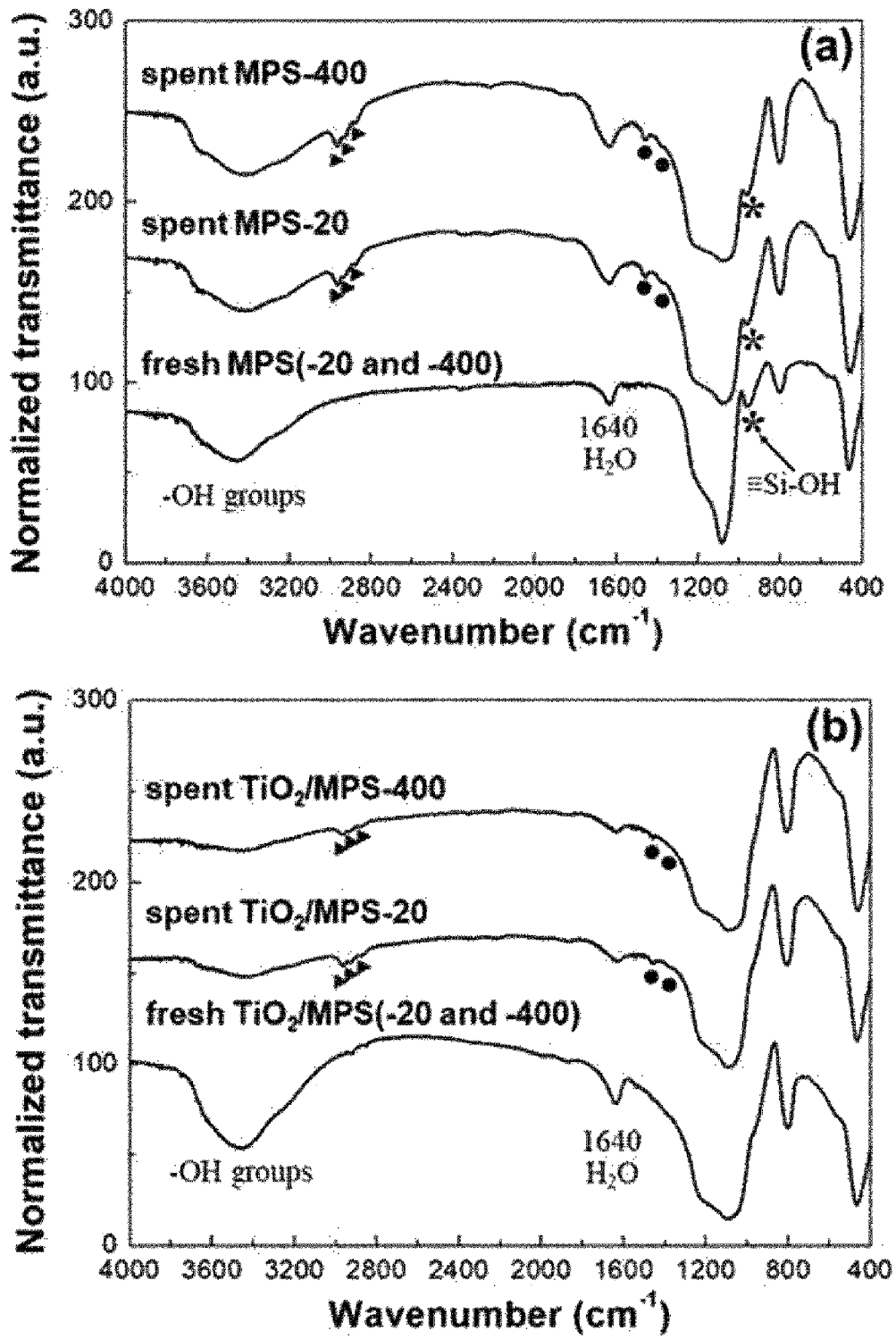
FIG. 16 shows FT-IR spectra of (a) MPS samples and (b) $TiO_2$/MPS samples. ▶, ●, and * indicate a C—H stretching mode in alkane, a C—H bending mode in alkane, and ≡Si—OH, respectively.

FIG. 16 shows FT-IR spectra of spent samples and fresh samples. In the spectra, characteristic bands were observed in three different regions. While the band observed near 960 cm$^{-1}$ was clearly observed in the spectrum of MPS samples, the band was relatively broader and difficult to identify in the spectrum of the TiO$_2$-impregnated samples. The band represents surface silanol groups, and the broadening of the band may be due to perturbation of the surface silanol groups by impregnated TiO$_2$ NPs. It was confirmed that the bands observed in the C-H stretching (2,876 cm$^{-1}$, 2,935 cm$^{-1}$, and 2,965 cm$^{-1}$) and C-H bending (1,382 cm$^{-1}$ and 1,457 cm$^{-1}$) regions were coke or tar-like heavy hydrocarbons deposited on the samples. In the spectra of spent TiO$_2$/MPS, the bands from the deposition of coke- and tar-like materials were significantly weakened compared to the spectra of the spent MPS samples. These results are in good agreement with those of TG/DTA. Among the spectra of spent samples, a small band observed at 2,200 cm$^{-1}$ could be designated as a cyano group (—CN). The cyano group could be generated by a chemical reaction between CH$_4$ and N$_2$ during plasma discharge, and could be included in the deposited carbonaceous materials of the spent samples. The observation of the N 1s peak in the XPS spectra (hereinafter, Example 4) of the spent samples is in good agreement with the results of FT-IR spectroscopy analysis.

Experimental Example 3: Method of DFT Calculation

To confirm the effects of anatase TiO$_2$ nanoparticles on coking phenomena by dehydrated methyl radials, calculation of density functional theory (DFT) and projected augmented wave (PAW) potential were performed using Vienna Ab Initio Simulation Package (VASP). In a test of spin-polarization, the energy difference between the spin-polarized and spin-depolarized results with respect to pure anatase TiO$_2$ and that onto which methyl radicals were adsorbed was negligible. Therefore, spin-polarization was excluded from this calculation. Considering the exchange-correlation in the Kohn-Sham theory, the Perdew-Burke-Ernzerhof (PBE) function based on a generalized gradient approximation (GGA) was used. In all of the calculations, the plane-wave was limited to a cutoff energy of 400 eV. Electronic occupancies were calculated using the Gaussian smearing with a smearing parameter of 0.05 eV. For bulk optimization, all of the internal atoms were relaxed in all directions. For a slab model, two bottom layers were fixed. A force-based conjugate gradient algorithm was used until the force applied to each atom was present within 0.03 eV/Å. For the Brillouin zones of optimization of bulk, plates, and separated gas-phase molecules, 5×5×2, 2×2×1, and 1×1×1 Monkhorst-Pack k-point sampling were used, respectively. The optimized lattice constants of anatase TiO$_2$ were 3.80 Å and 9.75 Å for the a- and c-axes, respectively. As shown in FIG. 14a, 6 layers (2 fixed layers and 4 relaxed layers) were used for the slab model. Each layer consisted of 1×2 supercells.

As shown in FIG. 14a, the (101) surface of anatase TiO$_2$ has 2c oxygen and 3c oxygen (O$_{2c}$, O$_{3c}$). In the calculations of adsorption and dehydration, an O$_{2c}$ top, an O$_{3c}$ top, an O$_{2c}$ bridge (between O$_{2c}$ and bonded Ti), an O$_{3c}$ bridge (between O$_{3c}$ and bonded Ti), and hollow (center of two O$_{2c}$ and two O$_{3c}$) sites were used for methyl and hydrogen radicals.

Since it is difficult to accurately define a gaseous radical, the relative stability of the adsorbed radicals was calculated using the chemical potential of H$_2$ molecules as follows:

$$E_{stability-CH_x} = E_{CH_x-slab} - E_{CH_3-slab} + \frac{3-x}{2}\mu_{H_2}$$

In particular, E$_{stability-CHx}$ represents the relative stability of adsorbed CH$_x$ radicals with respect to CH$_3$ radicals; E$_{CHx-slab}$ represents the total energy of CH$_x$ radicals adsorbed to the (101) facet of anatase TiO$_2$; and $\mu_{H2}$ represents a chemical potential of separated H$_2$ molecules.

Dehydration energy (Edehyd) was calculated as follows:

$$E_{dehyd} = E_{CHx-slab} - E_{CHx-1-slab} - E_{H-slab}$$

In particular, E$_{CHx-slab}$ and E$_{H-slab}$ represent the total energy of CH$_x$ radicals and H radicals adsorbed to the (101) facet of anatase TiO$_2$, respectively.

Example 4: XPS Results

Figure 17:
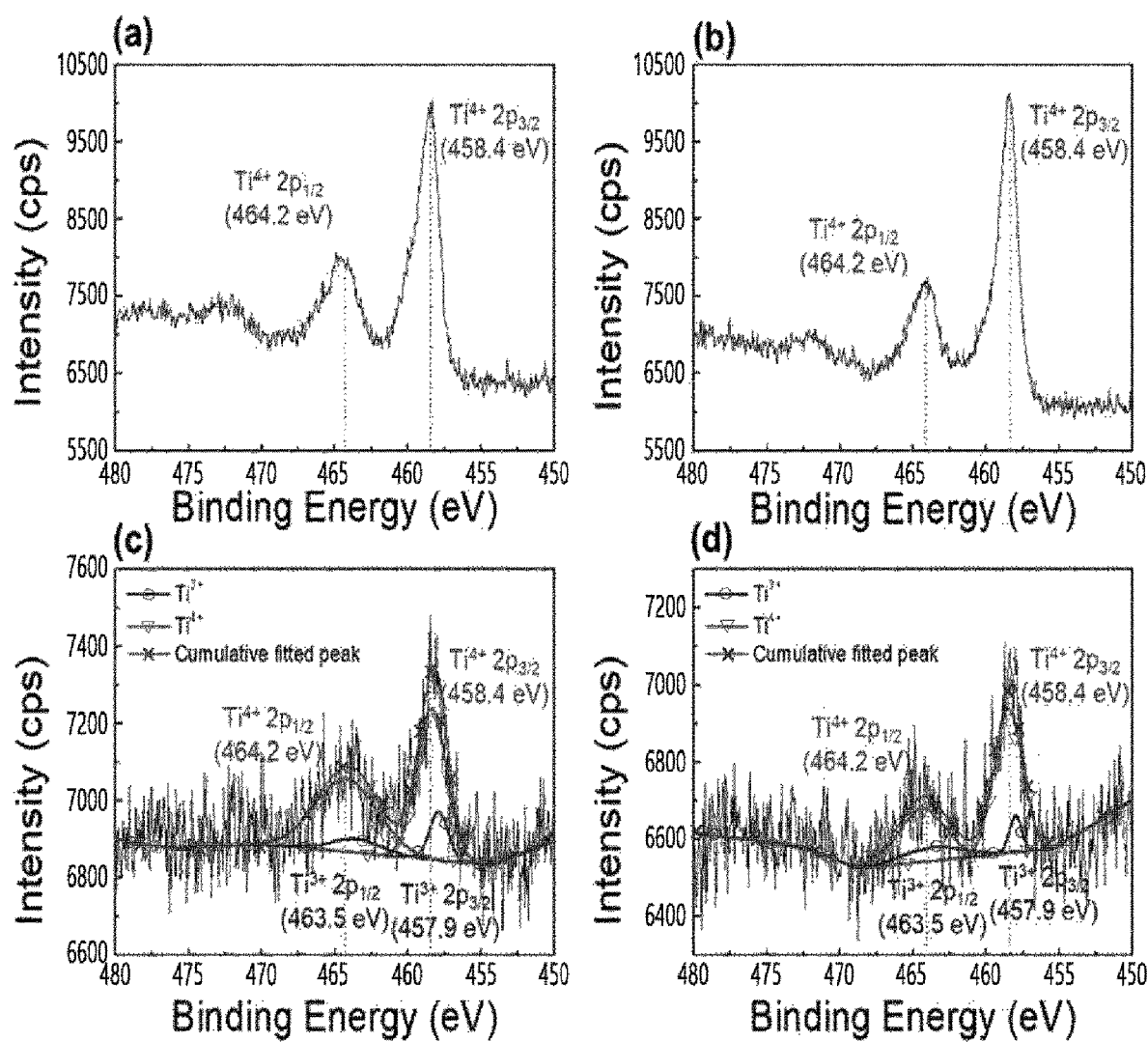
FIG. 17 shows HR-XPS spectra of (a) fresh $TiO_2$/MPS-20, (b) fresh $TiO_2$/MPS-400, (c) spent $TiO_2$/MPS-20, and (d) spent $TiO_2$/MPS-400 of Ti 2p.

In order to more specifically confirm the oxidation state of the spent samples after a plasma reaction, an XPS analysis was performed and the results were compared with those for the fresh samples. FIG. 17 shows the HR-XPS spectra of Ti 2p of fresh and spent TiO$_2$/MPS-20 and spent TiO$_2$/MPS-400 samples. It was confirmed that impregnated TiO$_2$ NPs were covered due to the deposited carbonaceous materials and that the peaks of Ti 2p$_{1/2}$ and Ti 2p$_{3/2}$ were significantly reduced compared to spent TiO$_2$/MPS-20 and spent TiO$_2$/MPS-400 (FIG. 18c and FIG. 18d). Therefore, for more specific confirmation, high-resolution XPS (HR-XPS) analysis was performed.

In all spectra, two peaks were observed at 458.4 eV and 464.2 eV, and these peaks may be due to the presence of Ti-O bonds of Ti$^{4+}$ species in the lattice of TiO$_2$ NPs. Meanwhile, the spectra of the spent samples were shown to be more complicated compared to those of the fresh samples. The spectra of the spent samples must be overlapping with two to three characteristic peaks. Therefore, a deconvolution technique was performed on the spectra of the spent samples (FIGS. 17c and 17d). In the deconvoluted spectra of the spent samples, two additional peaks representing the Ti$^{3+}$ species in Ti$_2$O$_3$ were observed (457.9 eV and 463.5 eV). Bharti et al. reported based on the XPS analysis of Ti 2p and O 1s spectra that the portions of Ti$^{3+}$ species reduced from a Ti$^{4+}$ species and oxygen vacancies were increased significantly on the surface of plasma-treated TiO$_2$ thin films after a plasma reaction (*Sci. Rep.*, 6 (2016) 32355; *Appl. Surf Sci.*, 364 (2016) 51-60). Further, it was concluded that the Ti$^{3+}$ species reduced from a Ti$^{4+}$ species on the surface of TiO$_2$ and oxygen vacancies can be generated in a greater amount by UV irradiation formed in the plasma or the bombardment of energetic ions in the plasma.

Figure 19:
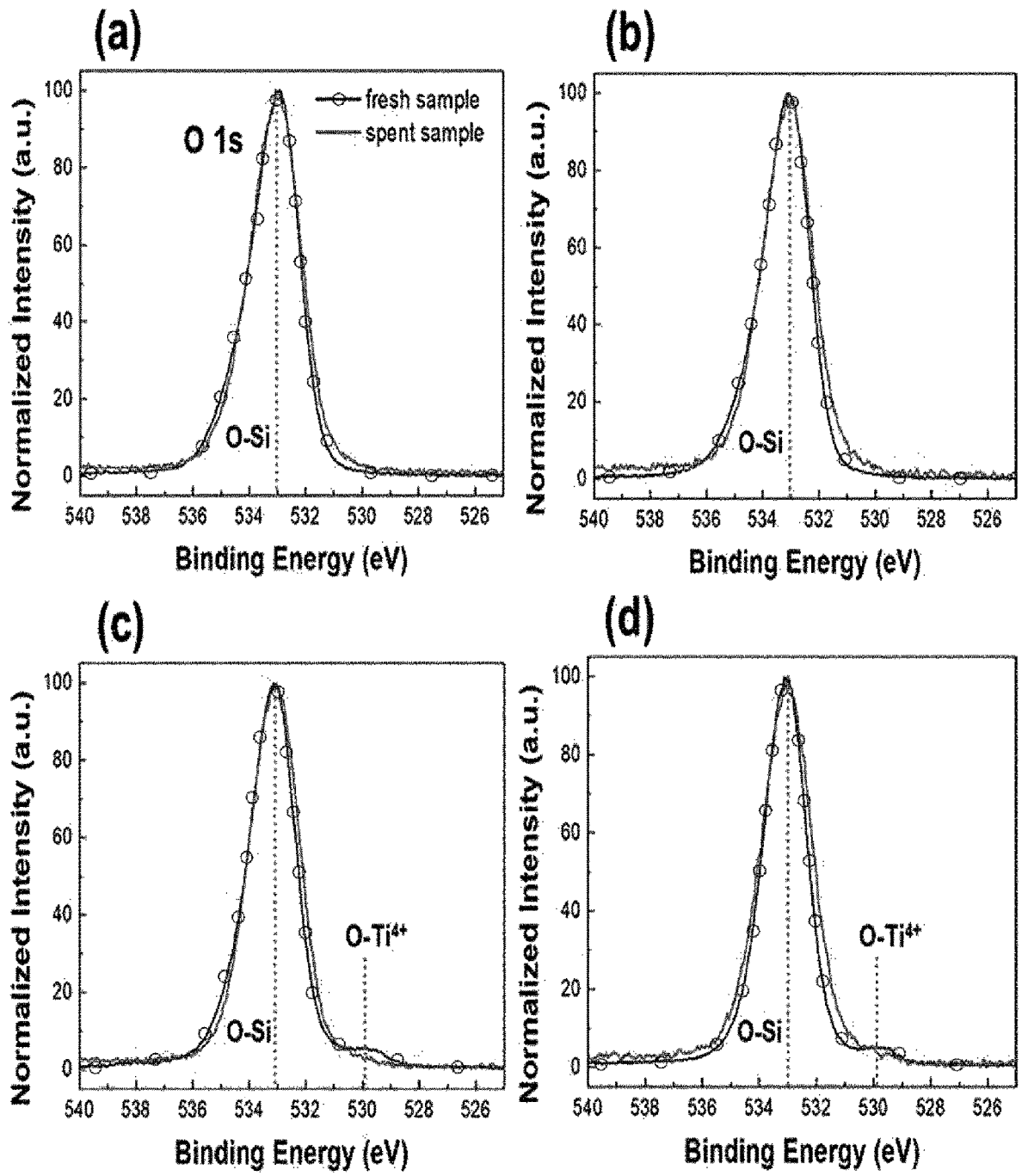
FIG. 19 shows HR-XPS spectra of fresh samples and spent samples of (a) MPS-20, (b) MPS-400, (c) $TiO_2$/MPS-20, and (d) $TiO_2$/MPS-400 of O 1s. The solid line with open circles and the bare solid line indicate spectra of fresh samples and spent samples, respectively.

FIG. 19 shows HR-XPS spectra of O 1s of fresh samples and spent samples. For the accurate comparison of the spectra between the fresh samples and spent samples, the intensities of all spectra were normalized to the peak intensity at 533.1 eV. In the spectra of fresh MPS-20 and MPS-400 (black lines in FIGS. 19a and 19b), the peak which represents the Si-O binding of amorphous $SiO_2$ was observed at the binding energy (BE) of 533.1 eV. Meanwhile, an additional peak, which represents the $O-Ti^{4+}$ binding of a lattice oxygen in the anatase $TiO_2$ lattice in the BE of 529.9 eV, was observed in the spectra of fresh $TiO_2$/MPS-20 and $TiO_2$/MPS-400 (black lines in FIGS. 19c and 19d). With respect to the spectra of the spent $TiO_2$/MPS-20 and $TiO_2$/MPS-400 (red lines in FIGS. 19c and 19d), the peak at 529.9 eV BE was shown to disappear or become broadened, whereas the peak in the spectrum of the fresh $TiO_2$/MPS sample was clearly shown. These results indicate that $Ti^{4+}$ in $TiO_2$ NPs was reduced and oxygen vacancies were generated.

Figure 18:
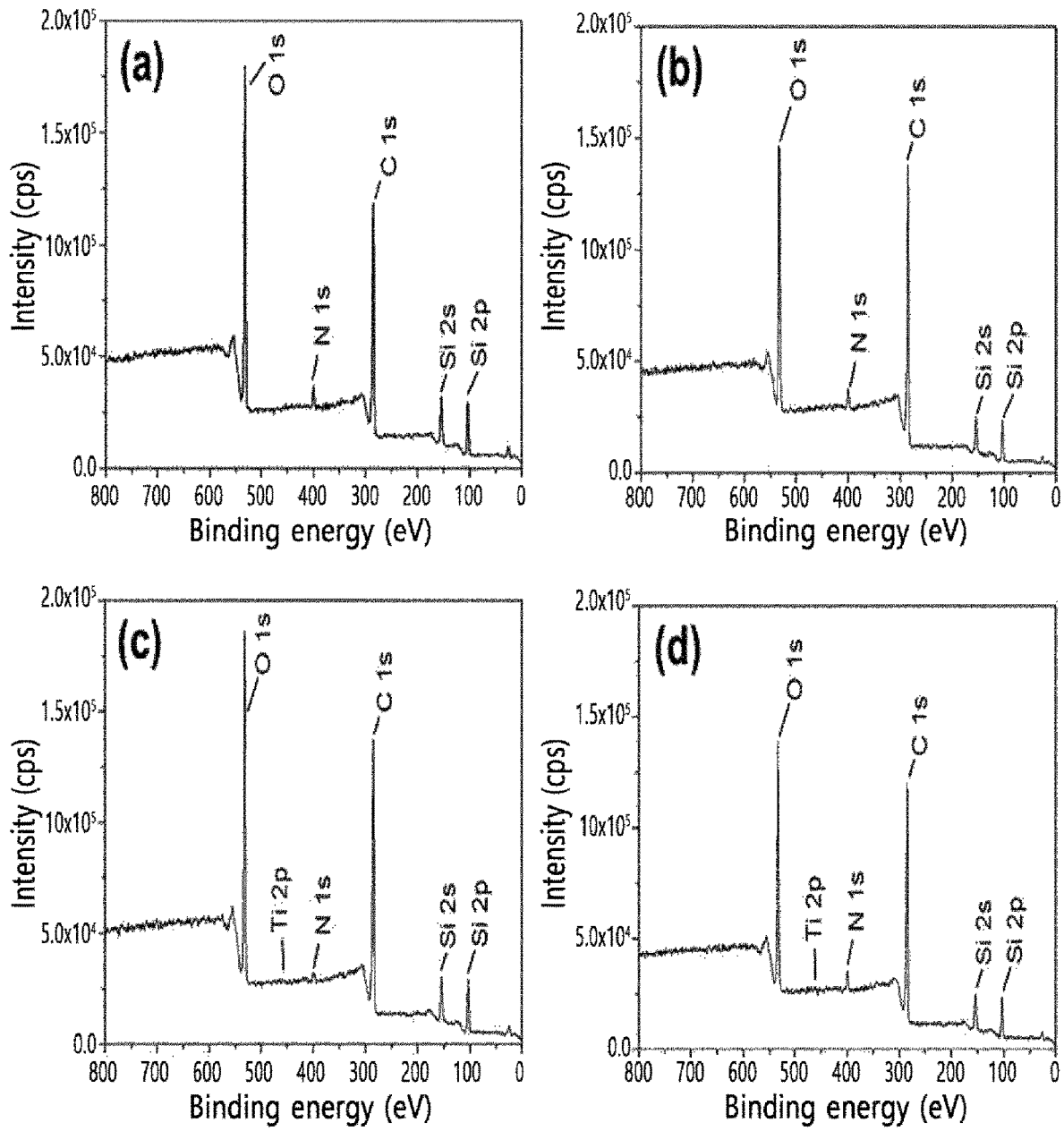
FIG. 18 shows XPS survey spectra of (a) spent MPS-20 and (b) spent MPS-400; and XPS survey spectra of (c) spent $TiO_2$/MPS-20 and (d) spent $TiO_2$/MPS-400.

FIG. 8 and FIG. 18 represent the entire spectra of each of the fresh and spent samples. In the spectra of fresh MPS-20 and MPS-400 (FIGS. 8a and 8b), dominant peaks were observed in the O 1s, Si 2s, and Si 2p regions. In the spectra of fresh $TiO_2$/MPS-20 and $TiO_2$/MPS-400 (FIGS. 8c and 8d), additional peaks of Ti $2p_{1/2}$ and Ti $2p_{3/2}$ were observed due to impregnated $TiO_2$ NPs. The small peak in the C 1s region observed in all of the spectra may be due to carbonaceous impurities generated during the XPS analysis. In the spectra of all of the samples (FIG. 18), the intensity of the C 1s peak was increased in size due to deposition of a carbonaceous material on the sample. As described above, a small peak of N 1s was observed in all of the spectra of the spent samples. However, the intensity of the N 1s peak was much lower than that of C 1s in all cases, and this indicates that the chemical reaction between $CH_4$ and $N_2$ is very minor in the entire plasma-induced methane coupling reaction. This observation of the N-containing chemical species is in good agreement with the results of FT-IR spectroscopic analysis confirmed previously.

CONCLUSION

Light hydrocarbons, in particular ethane, could be successfully synthesized by the DBD plasma technology. It was analyzed that the ethane fraction could reach about 80% by introducing macroporosity, and this is a significantly higher value by 20% to 30% compared to the values in the cases of alpha alumina and KIT-6 powder particles. Such a high fraction was also found in $C_3$ and $C_4$ hydrocarbons. In addition, the amount of a dielectric material required for the bed could be significantly reduced without compromising performance.

The formation of carbon deposit was effectively reduced by the use of titania nanoparticles in the matrix of a macroporous silica material. Due to the photocatalyst activity of $TiO_2$ nanoparticles, coke was produced in a lesser amount, while long-chain hydrocarbons were produced in a greater amount. Such a method can be used as a tool to reduce the amount of coke, especially during the course of the reaction. Such resistance to deactivation was demonstrated by analytical methods such as GC, TG/DTA, and HR-XPS. The DBD plasma reactor can be applied in various forms of commercial ethane cracking centers, and consequently can significantly increase the yield of $C_2$ hydrocarbons.

From the foregoing, one of ordinary skill in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A dielectric barrier discharge (DBD) plasma reactor for performing the conversion of methane to C2+ hydrocarbons comprising paraffin and olefins, the dielectric barrier discharge (DBD) plasma reactor comprising:
   a dielectric tube;
   macroporous silica disposed inside the dielectric tube;
   catalyst that is impregnated in pores of the macroporous silica;
   a ground electrode, which encompasses the whole or a part of a region of the dielectric tube in which the macroporous silica is disposed; and
   a powered electrode that is inserted in the macroporous silica, the powered electrode being spaced apart from an inner wall of the dielectric tube,
   wherein said dielectric tube is made of alumina;
   wherein the macroporous silica has pores with an average size of 1 μm to 10 μm and is in the form of a non-pelletized particle with an average diameter of 100 μm to 1,000 μm;
   wherein the DBD plasma is discharged by applying a power of 30 W to 60 W;
   wherein the powered electrode is connected to an alternating current (AC) power supply;
   wherein the macroporous silica is configured to prevent a pressure difference from forming inside the dielectric tube when a non-oxidative reaction of methane in the DBD plasma reactor is performed at room temperature and ambient pressure and is disposed between a first side and a second side of the dielectric tube, a gas inlet for impregnating methane is coupled to the first side of the dielectric tube, and a gas outlet is coupled to the second side of the dielectric tube;
   wherein the methane as a reactant is impregnated as a mixture with an inert gas at a ratio of 1:9 to 7:3 to reduce a coke formation;
   wherein a paraffin content in the C2+ hydrocarbons comprising paraffin and olefins is increased; and
   wherein the catalyst includes photocatalyst nanoparticles being contained in an amount of 0.5 wt % to 50 wt % of total filler weight, and shows that the coke formation is reduced or a fraction of C5+ hydrocarbons in C2+ hydrocarbons being produced is increased, compared to a reaction performed by using a reactor in which photocatalyst nanoparticles are not contained under the same reaction conditions as well as the maximum temperature required to remove coke formed in a conversion of methane to C2+ hydrocarbons by the DBD plasma reactor is lowered compared to using a reactor comprising no photocatalyst nanoparticles under the same reaction conditions.

* * * * *